United States Patent [19]
Lubisch et al.

[11] Patent Number: 5,852,017
[45] Date of Patent: Dec. 22, 1998

[54] 2,3(1H,4H)-QUINOXALINEDIONES

[75] Inventors: Wilfried Lubisch, Mannheim; Berthold Behl, Ludwigshafen; Hans Peter Hofmann, Limburgerhof, all of Germany

[73] Assignee: BASF Aktiengesellschaft, Ludwigshafen, Germany

[21] Appl. No.: 880,507

[22] Filed: Jun. 23, 1997

Related U.S. Application Data

[63] Continuation of Ser. No. 512,282, Aug. 8, 1995, Pat. No. 5,714,489, which is a continuation of Ser. No. 261,873, Jun. 17, 1994, abandoned, which is a continuation of Ser. No. 67,873, May 27, 1993, abandoned.

[30] Foreign Application Priority Data

May 30, 1992 [DE] Germany ............ 42 17 952.1

[51] Int. Cl.$^6$ ................................................ A61K 31/495
[52] U.S. Cl. ............................................. 514/249; 544/354
[58] Field of Search .............................................. 514/249

[56] References Cited

PUBLICATIONS

Corbett et al, *Drug Development Research*, 24 pp. 201–205, 1991.
Lipton, *Tins 16*, pp. 527–532, 1993.
Doble, *Therapie 50*, pp. 319–337, 1995.
Lees, *Pharmacology and Pathophysiology 5* pp. 51–74, 1996.

*Primary Examiner*—Emily Bernhardt
*Attorney, Agent, or Firm*—Keil & Weinkauf

[57] ABSTRACT

2,3(1H,4H)-quinoxalinediones of the formula I

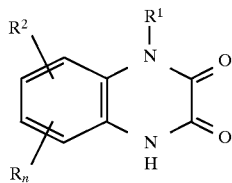

where $R^1$ is hydrogen, an aliphatic radical which has up to 12 carbons and can be substituted by one of the following: phenyl, cyclopentyl, cyclohexyl or —CO—$R^3$, —CO—O—$R^3$ or —CO—NH—$R^3$, where $R^3$ is hydrogen, $C_1$–$C_4$-alkyl, phenyl, benzyl or 1-phenylethyl, a cycloaliphatic radical with up to 12 carbons or phenyl, where the cyclic groups in $R^1$ can have up to three of the following substituents: $C_1$–$C_4$-alkyl, $C_1$–$C_4$-haloalkyl, $C_1$–$C_4$-alkoxy, $C_1$–$C_4$-haloalkoxy, halogen, nitro, cyano, —CO—O—$R^3$ and —CO—NH—$R^3$;

$R^2$ is 1-pyrrolyl which can have up to two of the following substituents: $C_1$–$C_4$-alkyl, phenyl, phenylsulfonyl, nitro, cyano and —CO—O—$R^3$, —CO—NH—$R^3$, —$CH_2$—O—$R^3$, —O—$R^3$ and —CH=NO—$R^3$ R radicals are identical or different and are the following: $C_1$–$C_4$-alkyl, $C_1$–$C_4$-alkoxy, trifluoromethyl, trichloromethyl, trifluoromethoxy, trichloromethoxy, fluorine, chlorine, bromine, iodine, nitro, cyano and —CO—O—$R^3$ and —CO—NH—$R^3$ as well as a fused-on benzene ring;

n is 0–3, and 2,3(1H,4H)-quinoxalinediones I'

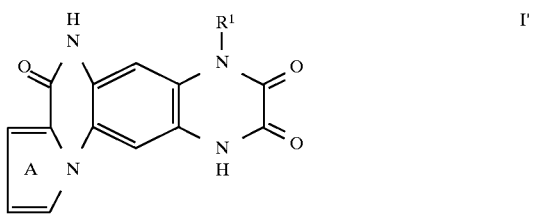

where $R^1$ has the stated meanings, are suitable as drugs in the treatment of neurodegenerative disorders and neurotoxic disturbances of the central nervous system.

2 Claims, No Drawings

2,3(1H,4H)-QUINOXALINEDIONES

This Application is a continuation of application Ser. No. 08/512,282, filed Aug. 8, 1995, now U.S. Pat. No. 5,714,489, which is a continuation application of Ser. No. 08/261,873, filed on Jun. 17, 1994, abandoned, which is a continuation of application Ser. No. 08/067,873, filed on May 27, 1993, abandoned.

The present invention relates to novel 2,3(1H,4H)-quinoxalinediones of the formula I

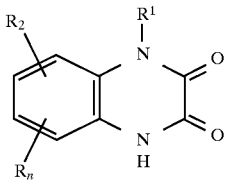

and their tautomers and enantiomers, as well as their physiologically tolerated salts, where $R^1$ is hydrogen, a cycloaliphatic radical having up to 8 carbons, phenyl, an aliphatic radical which has up to 12 carbons and can carry one or two identical or different substituents selected from phenyl, cyclopentyl, cyclohexyl, —CO—$R^3$, —CO—O—$R^3$, —CO—NH—$R^3$, —O$R^3$, —N$R^7R^3$,

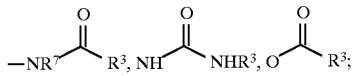

=N—O$R^3$, —CN where $R^3$ and $R^7$ are each, independently of one another, hydrogen, $C_1$–$C_4$-alkyl, phenyl, benzyl, 1-phenylethyl or 2-phenylethyl, and where the aliphatic and aromatic rings present in $R^1$ can carry up to three identical or different substituents selected from the following: $C_1$–$C_4$-alkyl, $C_1$–$C_4$-haloalkyl, $C_1$–$C_4$-alkoxy, $C_1$–$C_4$-haloalkoxy, halogen, nitro, cyano, —CO—O$R^9$, —CO—NH—$R^9$, —OH,

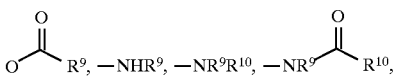

=N—O$R^9$, =O;

where $R^9$ and $R^{10}$ are each, independently of one another, hydrogen, $C_1$–$C_4$-alkyl, phenyl, benzyl, 1-phenylethyl and 2-phenylethyl, $R^2$ is 1-pyrrolyl which can carry one or two of the following substituents: $C_1$–$C_4$-alkyl, phenyl, phenylsulfonyl, nitro, cyano or
—CO—O—$R^3$, —CO—NH—$R^3$, —CH$_2$—O—$R^3$, —O—$R^3$, —CH=NO—$R^3$, —C(O)$R^3$,

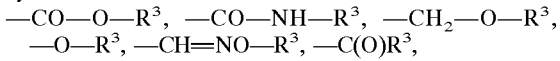

—CH=CH—$R^8$, —CH=N—$R^3$, where $R^8$ can be —COO$R^3$, —CONH—$R^3$, CN or phenyl;

R radicals are identical or different and are the following: $C_1$–$C_4$-alkyl, $C_1$–$C_4$-alkoxy, trifluoromethyl, trichloromethyl, trifluoromethoxy, trichloromethoxy, fluorine, chlorine, bromine, iodine, nitro, cyano or —CO—O—$R^3$, —CO—NH—$R^3$, —SO$_2R^3$

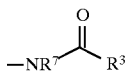

as well as a fused-on benzene ring which in turn can carry up to three of the radicals mentioned for R;

n is an integer from 0 to 3, but is 0 or 1 in the presence of the fused-on benzene ring.

The present invention further relates to 2,3(1H,4H)-quinoxalinediones of the formula I'

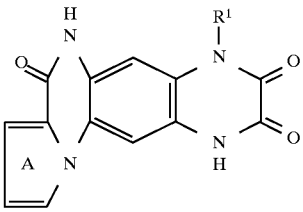

and their tautomers and enantiomers, as well as their physiologically tolerated salts, where $R^1$ has the meaning specified in claim 1, and where ring A can be substituted as mentioned in claim 1 for 1-pyrrolyl.

The present invention additionally relates to processes for preparing the compounds I and I' and to the use thereof as drugs in human and veterinary medicine.

Derivatives of 2,3(1H,4H)-quinoxalinedione

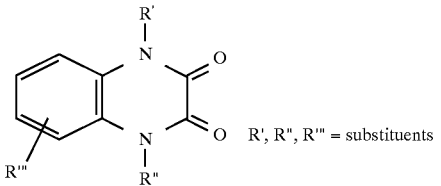

R', R'', R''' = substituents are proposed in numerous publications for the treatment of disorders of the central nervous system and as hypnotics and sedatives. For example, EP-A 315 959, EP-A 374 534 and EP-A 377 112 describe compounds in which R''' is halogen, nitro, cyano, hydroxyl, trifluoromethyl, $C_1$–$C_4$-alkoxy and —SO$_2$H, —SO$_2R^x$, —SONH$_2$, —SO$_2$NHR$^x$ and —SO$_2$NR$_2^x$ where $R^x$ is $C_1$–$C_4$-alkyl, as well as a fused-on benzene ring, which can also be substituted. R''' in U.S. Pat. No. 3,992,378 is $C_1$–$C_2$-fluoroalkyl, and in PCT 91/13878, besides halogen and nitro, is $C_1$–$C_6$-alkyl, alkoxy, aryloxy and aralkoxy.

Furthermore, EP-A 8864 mentions piperidinyl, pyrrolidinyl and piperazinyl as R'''. Compounds of the latter type are also disclosed in Ind. J. Chem. 28B (1989), 888–890; also mentioned therein is an examination of their utilizability for the control of hookworms and tapeworms, which showed that these compounds are unsuitable.

The known compounds have the disadvantage that their ability to overcome the blood-brain barrier is only poor or nonexistent, and their effect is therefore unsatisfactory.

It is an object of the present invention to find novel, more effective 2,3(1H,4H)-quinoxalinediones, their tautomers and enantiomers, and their physiologically tolerated salts.

We have found that this object is achieved by the compounds I and I' defined at the outset.

We have also found various processes, which are described in detail hereinafter, for preparing the 2,3(1H,4H)-quinoxalinediones I and I', as well as the use thereof as drugs in human and veterinary medicine.

The meanings of the variables in the compounds I and I' are as follows:

$R^1$ hydrogen, an aliphatic radical with up to 12 carbons, such as methyl, ethyl, n-propyl, isopropyl, n-butyl, isobutyl, sec-butyl, tert-butyl, n-pentyl, tert-amyl, 1-methylbutyl, 2,2-dimethylpropyl, n-hexyl, 1-methylpentyl, 1,1-dimethylbutyl, 1,1,2-trimethylpropyl, 1-ethyl-1-methylpropyl, 2,2-diethylethyl, n-heptyl, 1-methylhexyl, 1,1-dimethylpentyl, 1-ethyl-1-methylbutyl, 1,1-diethylpropyl, 1-methyl-1-propylpropyl, 1-ethyl-1-propethyl, 1-methyl-1-butylethyl, 1,1,2,2-tetramethyl1-propyl, n-octyl, 1,1-dimethylhexyl, 1-ethyl-1-methylpentyl, 1,1-diethylbutyl, 1-methyl-1-propylbutyl, 1-ethyl-1-propylpropyl, 1,1,3,3-tetramethylbutyl, 1,1-dimethylheptyl, 1,1-dimethyloctyl, 1,1-dimethylnonyl and 1,1-dimethyldecyl, which can have one of the following substituents: phenyl, cyclopentyl, cyclohexyl or —CO—$R^3$, —CO—O—$R^3$ or —CO—NH—$R^3$, where $R^3$ is hydrogen, methyl, ethyl, n-propyl, isopropyl, n-butyl, isobutyl, sec-butyl, tert-butyl, phenyl, benzyl or 1-phenylethyl;

a cycloaliphatic radical with up to 12 carbons, such as cyclopropyl, cyclobutyl, cyclopentyl, cyclohexyl, cycloheptyl, cyclooctyl, cyclononyl, cyclodecyl, cycloundecyl, cyclododecyl, 2-oxocyclopentyl, 2-oxocyclohexyl, 2-oxocyclooctyl and the corresponding unsaturated cycloaliphatic radicals or phenyl, where the cyclic groups in $R^1$ can have up to three of the following substituents: $C_1$–$C_4$-alkyl such as methyl, ethyl, n-propyl, isopropyl, n-butyl, isobutyl, sec-butyl, tert-butyl, $C_1$–$C_4$-alkoxy such as methoxy, ethoxy, n-propoxy, isopropoxy, n-butoxy, isobutoxy, sec-butoxy, tert-butoxy, $C_1$–$C_4$-haloalkyl, $C_1$–$C_4$-haloalkoxy, halogen, nitro, cyano, CO—O—$R^3$ and —CO—NH—$R^3$;

$R^2$ 1-pyrrolyl which can have up to two of the following substituents: methyl, ethyl, n-propyl, isopropyl, n-butyl, isobutyl, sec-butyl, tert-butyl, phenyl, phenylsulfonyl, nitro, cyano and —CO—O—$R^3$, —CO—NH—$R^3$, —$CH_2$—O—$R^3$, —O—$R^3$ and —CH=NO—$R^3$ R radicals, which are identical or different: methyl, ethyl, n-propyl, isopropyl, n-butyl, isobutyl, sec-butyl, tert-butyl, $C_1$–$C_4$-alkoxy, trifluoromethyl, trichloromethyl, trifluoromethoxy, trichloromethoxy, fluorine, chlorine, bromine, iodine, nitro, cyano and —CO—O—$R^3$ and —CO—NH—$R^3$ as well as a fused-on benzene ring which in turn can have up to 3 of the radicals mentioned for R;

n 0 to 3.

Alkyl in haloalkyl or haloalkoxy is methyl, ethyl, propyl, isopropyl, butyl, isobutyl, sec-butyl or tert-butyl.

Halogen, or halogen in haloalkyl or haloalkoxy is fluorine, chlorine, bromine or iodine.

In particularly preferred compounds $R^1$ is hydrogen, methyl, ethyl, n-propyl, isopropyl, n-butyl, isobutyl, sec-butyl or tert-butyl, —$(CH_2)_m$—$R^4$ where m is from 0 to 2 and $R^4$ is cyclohexyl or phenyl which can be substituted by fluorine, chlorine, bromine, nitro, trifluoromethyl, trifluoromethoxy, methyl, ethyl, n-propyl, isopropyl, n-butyl, isobutyl, sec-butyl or tert-butyl, or —$CHR^5$—$(CH_2)_m$—CO—O—$R^6$ or —$CHR^5$—$(CH_2)_m$—CO—NH—$R^6$ where $R^5$ is hydrogen, methyl, ethyl, n-propyl, isopropyl, n-butyl, isobutyl, sec-butyl or tert-butyl and $R^6$ is $R^5$ or —$(CH_2)_m$—$R^4$, especially hydrogen and cyclohexyl, $R^2$ is 1-pyrrolyl which can have up to two of the substituents $C_1$–$C_4$-alkyl, $C_1$–$C_4$-alkoxy, phenyl, formyl, acetyl, propionyl and —CO—O—$R^6$ and —CO—NH—$R^6$, especially 1-pyrrolyl, 2,5-dimethyl-1-pyrrolyl, 2-methoxy-1-pyrrolyl, 2,5-diphenyl-1-pyrrolyl, 2-formyl-1-pyrrolyl, 2-propionyl-1-pyrrolyl, 2-carboxy-1-pyrrolyl and 2-methoxycarbonyl-1-pyrrolyl, R is methyl, ethyl, n-propyl, isopropyl, n-butyl, iso-butyl, sec-butyl, tert-butyl, fluorine, chlorine, bromine, nitro, trifluoromethyl, trifluoromethoxy or a fused-on benzene ring which in turn can carry a radical mentioned for R, especially chlorine, nitro, trifluoromethyl and a fused-on benzene ring, and n is 0 or 1, with the proviso that n is 2 in the case of the fused-on benzene ring.

The compounds I according to the invention can in principle be prepared by two routes, by reacting an aminophenylene-1,2-diamine II

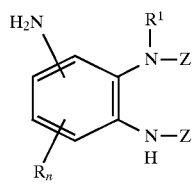

where Z is an acyl protective group, with succinaldehyde or its acyclic or cyclic acetal or hemiacetal (compound III) to give IV

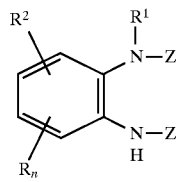

and, after elimination of the protective group Z, effecting the ring closure to I in a conventional manner with oxalic acid or one of its functional derivatives, or by initially converting II in unprotected form with oxalic acid or one of its functional derivatives into the corresponding amino-2,3(1H, 4H)-quinoxalinediones and then reacting the latter with III to give I.

Specifically, the compounds I according to the invention can be obtained in the following way: The starting material is an aminophenylene-1,2-diamine II in which Z is a protective acyl group, preferably acetyl or trifluoroacetyl, and which is reacted in a known manner, for example from A. R. Katritzky and C. W. Rees, "Comprehensive Heterocyclic Chemistry", Vol. 4, part 306, pages 313 et seq., in the presence of catalytic amounts of an acid, such as acetic acid, with a compound III, preferably the cyclic acetal, with elimination of water to give IV.

The acid can also act as solvent if used in larger amounts.

However, it is generally customary to carry out the reaction in a solvent such as toluene or in a mixed solvent such as toluene/dimethylformamide with acid catalysis at from 50° to 150° C., preferably 100° to 150° C.

After elimination of the protective group, the ring closure of IV is carried out in a conventional manner with oxalic acid or one of its functional derivatives, preferably oxalates such as dimethyl oxalate or diethyl oxalate, to give I. The temperature and time for the ring closure are generally known.

Aminophenylene-1,2-diamines II are disclosed or can be obtained as disclosed in, for example, U.S. Pat. No. 3,992, 378. They can also be prepared from commercially available o-phenylenediamines after introduction of protective groups in a conventional manner by nitration and subsequent reduction of the nitro group.

Another possibility for the preparation of the starting compounds II comprises the conventional reaction of 2-nitrochlorobenzenes with amines such as ethylamine, cyclohexylamine, 1-phenylethylamine and α-aminoacetates to give the corresponding 2-nitroanilines, subsequent reduction of the nitro group, introduction of protective groups, and nitration and reduction of the additional nitro group.

The reaction of 2-nitrochlorobenzenes with amines is conventionally carried out in polar solvents such as dimethylformamide, dimethyl sulfoxide and ethanol in the presence of basic salts such as potassium carbonate at from 25° to 180° C., preferably from 25° to 140° C.

The introduction and elimination of protective groups are carried out by conventional methods as described in, for example, T. W. Greene, "Protective Groups in Organic Synthesis", Wiley and Sons, New York 1982, Chapter 7, pages 249 et seq.

The nitration and reduction steps in the synthesis can be carried out by the conventional methods described in Houben-Weyl, "Methoden der organischen Chemie", Volume 10/1 and Volume 11/1 respectively. Suitable for the nitration are acetic acid/nitric acid and sulfuric acid/sodium nitrate mixtures.

The reduction can be carried out chemically or catalytically. In the catalytic variant, for example, the reduction is carried out with hydrogen on palladium/active carbon or platinum/active carbon in the presence of a solvent; the chemical reduction can be carried out with sodium borohydride/copper sulfate in dimethylformamide or in alcohols such as ethanol. It is also conventional to reduce the nitro groups with redox systems such as iron/hydrochloric acid and zinc/hydrochloric acid.

Another possibility for the preparation of the compounds I according to the invention comprises carrying out the steps in the synthesis described above, the reaction with III and the ring closure, in the reverse sequence.

The initial ring closure is carried out by reacting unprotected aminophenylene-1,2-diamine II with oxalic acid or one of its functional derivatives such as oxalyl chloride or oxalates by conventional methods to give the corresponding amino-2,3(1H,4H)-quinoxalinediones. Before the subsequent reaction with III to give I, it is advisable when further substituents R, for example nitro, are introduced into the aminoquinoxalinedione to protect the amino group with acyl in order then, after elimination of the protective group in the presence of hydrochloric acid, to react either the free amino-2,3(1H,4H)-quinoxalinediones or their hydrochlorides with III.

The compounds I' according to the invention are prepared by reducing the nitro group in a 2,3(1H,4H)-quinoxalinedione I"

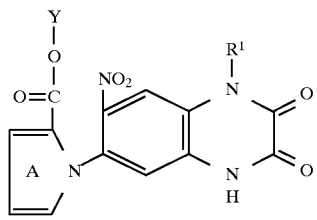

prepared by the process according to the invention described above. The reduction is carried out in a conventional way under acid conditions, for example with hydrogen on palladium/active carbon or glacial acetic acid/iron, with elimination of YOH where Y is hydrogen or $C_1$–$C_4$-alkyl, preferably methyl.

The pharmacological activity of the compounds I and I' according to the invention was investigated on membrane material isolated from rat cerebra. To do this, the membrane material was treated in the presence of the compounds according to the invention with the radio-labeled substances $^3$H-2-amino-3-hydroxy-5-methyl-4-isoxazolepropionic acid ($^3$H-AMPA) and $^3$H-5,7-dichlorokynurenic acid, which bind to specific receptors (AMPA and NMDA (N-methyl-D-aspartate) receptors respectively). The radioactivity of the treated membranes was then measured by scintillation counting. The amounts of bound $^3$H-AMPA and $^3$H-5,7-dichlorokynurenic acid, or the amounts of these radiolabeled substances displaced in each case, can be determined from the bound radioactivity. The resulting dissociation constant $K_I$ (I=inhibitor), which is a measure of the displacement by the active substance according to the invention, was calculated by iterative non-linear regression analysis with the statistical analysis system (SAS) on an IBM computer, similar to the "Ligand" program of P. J. Munson and D. Rodbard (Analytical Biochem. 107, (1980) 220, Ligand: Versatile Computerized Approach for Characterization of Ligand Binding Systems).

The following in vitro investigations were carried out:
1. Binding of $^3$H-2-amino-3-hydroxy-5-methyl-4-isoxazolepropionic acid ($^3$H-AMPA)

To prepare the membrane material, freshly removed rat cerebra were homogenized together with about 15 times the volume of a buffer solution A composed of 30 mM α, α, α-tris-(hydroxymethyl)methylamine hydrochloride (Tris-HCl) and 0.5 mM ethylenediaminetetraacetic acid (EDTA), pH 7.4, using an Ultra-Turrax. The suspension was centrifuged at 48,000×g for 20 minutes. The supernatant liquid was removed and then the protein-containing membrane material in the sediment was washed three times by suspension in buffer solution A followed by centrifugation at 48,000×g for 20 minutes each time. The membrane material was then suspended in 15 times the volume of buffer solution A and incubated at 37° C. for 30 minutes. The protein material was subsequently washed twice by centrifugation and suspension and stored at −70° C. until used.

For the binding assay, the protein material was thawed at 37° C. and washed twice by centrifugation at 48,000×g (20 minutes) followed by suspension in a buffer solution B composed of 50 mM Tris-HCl, 0.1M potassium thiocyanate and 2.5 mM calcium chloride, pH 7.1. Subsequently, 0.25 mg of membrane material, 0.1 μCi of $^3$H-AMPA (60 Ci/mmol) and compound I or I' were dissolved in 1 ml of buffer solution B and incubated on ice for 60 minutes. The incubated solution was filtered through a CF/B filter (Whatman) which had previously been treated for at least 2 hours with a 0.5% strength aqueous solution of polyethyleneimine. The filtrate was then washed with 5 ml of cold buffer solution B to separate bound and free $^3$H-AMPA. The radioactivity of the $^3$H-AMPA bound in the membrane material was measured by scintillation counting, and then the $K_I$ was determined by regression analysis of the displacement plots. The $K_I$ found for 7-chloro-6-(1-pyrrolyl)-2,3(1H,4H)-quinoxalinedione (Example 1) was <10 μM.

2. Binding of $^3$H-5,7-dichlorokynurenic acid

To prepare the membrane material, freshly removed rat cerebra were homogenized with about 10 times the volume of a buffer solution A' composed of 50 mM Tris-HCl and 10 mM EDTA, pH 7.4. The suspension was centrifuged at 48,000×g for 20 minutes. The supernatant liquid was removed, and the membrane material in the sediment was washed twice by suspension in buffer solution A' followed by centrifugation for 20 minutes each time. After renewed suspension of the membranes in buffer solution A' and freezing in liquid nitrogen, the suspension was thawed at 37° C. and, after a further wash, incubated at 37° C. for 15 minutes. The protein material was then washed four times by centrifugation and suspension and stored at −70° C. until used.

For the binding assay, the protein material was thawed at 37° C. and then washed twice by centrifugation at 48,000×g (20 minutes) followed by suspension in a buffer solution B' composed of 50 mM Tris-HCl, pH 7.4. Subsequently, 0.15 mg of membrane material, 0.3 $\mu$Ci of $^3$H-5,7-dichlorokynurenic acid (16 Ci/mmol) and compound I or I' were dissolved in 1 ml of buffer solution B' and incubated on ice for 30 minutes. The incubated solution was centrifuged at 150,000×g for 2 minutes. The supernatant liquid was removed and then the sediments were suspended twice with 1.5 ml of cold buffer solution B' each time. After measurement of the radioactivity of the $^3$H-5,7-dichlorokynurenic acid bound to the membranes in the sediment, the $K_I$ was found by regression analysis of the displacement plots. The $K_I$ found for 6-(1-pyrrolyl)-7-trifluoromethyl-2,3(1H,4H)-quinoxalinedione (Example 2) was <10 $\mu$M.

The compounds I and I' according to the invention are suitable as drugs in human and veterinary medicine and can be used to produce drugs for the treatment of neurodegenerative disorders and neurotoxic disturbances of the central nervous system and for producing spasmolytics, antiepileptics, anxiolytics and antidepressants.

The pharmaceutical compositions according to the invention contain a therapeutically effective amount of the compounds I and I' in addition to conventional pharmaceutical ancillary substances. For topical application, eg. in dusting powders and ointments, the active substances can be present in the conventional concentrations. As a rule, the contents of the active substances are from 0.0001 to 1% by weight, preferably 0.001 to 0.1% by weight.

For internal use, the preparations are administered in single doses. A single dose contains from 0.1 to 50 mg, preferably 0.1 to 10 mg, of active substance per kg of bodyweight. The compositions can be administered in one or more doses each day, depending on the nature and severity of the disorder.

Besides the active substance, the pharmaceutical compositions according to the invention contain conventional carriers and diluents appropriate for the required mode of administration. Pharmaceutical ancillary substances which can be used for topical application are ethanol, isopropanol, ethoxylated castor oil, ethoxylated hydrogenated castor oil, polyacrylic acid, polyethylene glycol, polyethylene glycol stearate, ethoxylated fatty alcohols, liquid paraffin, petrolatum and lanolin. Examples suitable for internal use are lactose, propylene glycol, ethanol, starch, talc and polyvinylpyrrolidone. It is also possible for antioxidants such as tocopherol and butylated hydroxyanisole and butylated hydroxytoluene, flavorings, stabilizers, emulsifiers and lubricants to be present.

The substances present in addition to the active substance in the composition, and the substances used in the production of the pharmaceutical composition, must be toxicologically acceptable and compatible with the relevant active substance.

The pharmaceutical compositions are produced in a conventional way, eg. by mixing the active substance with the other conventional carriers and diluents.

The pharmaceutical compositions can be administered in a variety of ways such as orally, parenterally, subcutaneously, intraperitoneally and topically. Thus, possible presentations are tablets, emulsions, solutions for infusion and injection, pastes, ointments, gels, creams, lotions, dusting powders and sprays.

EXAMPLE 1

7-Chloro-6-(1-pyrrolyl)-2,3(1H,4H)-quinoxalinedione a) Preparation of 3,4-diacetamido-1-chlorobenzene 28.4 g (0.2 mol) of 4-chloro-1,2-phenylenediamine were dissolved in 130 ml of 3 molar hydrochloric acid and diluted with 300 ml of water. 51 g (0.5 mol) of acetic anhydride were added dropwise and then the reaction mixture was stirred at room temperature for 30 minutes, 41 g (0.6 mol) of sodium acetate were added, and the mixture was extracted with ethyl acetate. Workup of the organic phase resulted in a yield of 21% of the product.

Melting point 216° C.

b) Preparation of 4,5-diacetamido-1-chloro-2-nitrobenzene

A solution of 5 g (22 mmol) of 3,4-diacetamido-1-chlorobenzene in 50 ml of concentrated sulfuric acid was cooled to 0° C., and 1.9 g (8.5 mmol) of sodium nitrate were added a little at a time, and the mixture was stirred at room temperature for 15 minutes. It was then poured into ice-water, and the crude product was filtered off with suction and washed with water. A yield of 63% of the product was obtained.

Melting point 232° C.

c) Preparation of 4,5-diacetamido-2-amino-1-chlorobenzene

To a solution of 4 g (14.7 mmol) of 4,5-diacetamido-1-chloro-2-nitrobenzene in 200 ml of ethanol were added a solution of 0.4 g of copper(II) sulfate×5H$_2$O in 2 ml of water and subsequently, a little at a time, 1.1 g (29.4 mmol) of sodium borohydride. The mixture was refluxed for 3 hours and subsequently filtered. The filtrate was concentrated, and the crude product was washed with water and methylene chloride. Workup of the organic phase gave a yield of 94% of the product.

Melting point 237° C.

d) Preparation of N-(2-chloro-4,5-diacetamidophenyl) pyrrole 3 g (12.4 mmol) of 4,5-diacetamido-2-amino-1-chlorobenzene and 1.6 g (12.4 mmol) of 2,5-dimethoxytetrahydrofuran in 150 ml of acetic acid were refluxed for 30 minutes. The reaction mixture was concentrated, the residue was washed with water and ethyl acetate, and the organic phase was worked up.

Yield: 81%

Melting point 206° C.

e) Preparation of N-(2-chloro-4,5-diaminophenyl)pyrrole

A solution 1.4 g (4.8 mmol) of N-(2-chloro-4,5-diacetamidophenyl)pyrrole and 0.4 g (9.8 mmol) of potassium hydroxide in 25 ml of ethylene glycol was stirred at 60° C. for 30 minutes. The reaction mixture was then poured into water, extracted with ethyl acetate and worked up.

Yield: 81%

Melting point: 206° C.

$^1$H-NMR (D$_6$-DMSO): δ (ppm): 2.6 (4H); 6.2 (2H); 7.5 (1H); 7.7 (1H)

f) Preparation of 7-chloro-6-(1-pyrrolyl)-2,3(1H,4H)-quinoxalinedione 0.6 g (2.9 mmol) of N-(2-chloro-4,5-diaminophenyl) pyrrole and 32 g (221 mmol) of diethyl oxalate were refluxed for 3 hours. The reaction mixture was cooled and then the crude product was filtered off and washed with petroleum ether.

Yield: 40%

Melting point >320° C.

$^1$H-NMR (D$_6$-DMSO): δ (ppm): 6.25 (2H); 6.95 (2H); 7.10 (1H); 7.25 (1H); 12.0 (2H)

EXAMPLE 2

6-(1-Pyrrolyl)-7-trifluoromethyl-2,3(1H,4H)-quinoxalinedione

This compound was prepared by the method of Example 1f from 0.8 g (3.3 mmol) of N-(2-trifluoromethyl-4,5-diaminophenyl)pyrrole and 32 g (221 mmol) of diethyl oxalate.

Yield: 43%

Melting point >300° C.

$^1$H-NMR (D$_6$-DMSO): δ (ppm): 6.2 (2H); 6.9 (2H); 7.0 (1H); 7.5 (1H); 12.5 (2H)

EXAMPLE 3

1-Cyclohexyl-6-trifluoromethyl-7-(1-pyrrolyl)-2,3 (1H,4H)-quinoxalinedione a) Preparation of N-cyclohexyl-2-nitro-4-trifluoromethylaniline A solution of 50 g (0.22 mol) of 2-nitro-4-trifluoromethyl-1-chlorobenzene, 22 g (0.22 mol) of cyclohexylamine and 61 g (0.44 mol) of potassium carbonate in 600 ml of ethanol was refluxed for 4 hours. The reaction mixture was concentrated and then the crude product was washed with water and ether. The organic phase was worked up, and the product was purified by column chromatography on silica gel (mobile phase:heptane/ethyl acetate=5/1).

Yield: 51%

Melting point 81° C.

b) Preparation of 2-cyclohexylamino-5-trifluoromethylaniline 32 g (0.11 mol) of N-cyclohexyl-2-nitro-4-trifluoromethylaniline dissolved in 250 ml of methanol were hydrogenated under a pressure of about 1 bar of hydrogen in the presence of 1.5 g of palladium/active carbon (10% by weight Pd) at room temperature. The reaction mixture was filtered. Conventional workup of the filtrate gave a 100% yield of the abovementioned compound.

Melting point 70° C.

c) Preparation of 1-cyclohexyl-6-trifluoromethyl-2,3(1H,4H)-quinoxalinedione 28 g (0.11 mol) of 2-cyclohexylamino-5-trifluoromethylaniline and 322 g (2.2 mol) of diethyl oxalate were refluxed for 2 hours. The reaction mixture was then concentrated, and the crude product was recrystallized from ethanol.

Yield: 59%

Melting point 183° C.

d) Preparation of 1-cyclohexyl-6-trifluoromethyl-7-nitro-2,3(1H,4H)-quinoxalinedione A solution of 20 g (64 mmol) of 1-cyclohexyl-6-trifluoromethyl-2,3(1H,4H)-quinoxalinedione in 400 ml of concentrated sulfuric acid was cooled to 0° C., 5.4 g (64 mmol) of sodium nitrate were added a little at a time over the course of one hour, and the mixture was stirred at room temperature for 3 hours. It was then poured into ice-water, and the crude product was filtered off with suction and recrystallized from methanol.

Yield: 78%

Decomposition point 272° C.

e) Preparation of 1-cyclohexyl-6-trifluoromethyl-7-amino-2,3(1H,4H)-quinoxalinedione 8 g (22.4 mmol) of 1-cyclohexyl-6-trifluoromethyl-7-nitro-2,3(1H,4H)-quinoxalinedione dissolved in 200 ml of tetrahydrofuran were hydrogenated under a pressure of about 1 bar of hydrogen in the presence of 1 g of palladium/active carbon (10% by weight Pd) at room temperature. The reaction mixture was filtered. Conventional workup of the filtrate gave a 100% yield of the abovementioned compound.

Decomposition point >260° C.

$^1$H-NMR (D$_6$-DMSO): δ (ppm): 1.4–1.6 (3H); 1.6–1.8 (3H); 1.8–2.0 (2H); 2.3–2.6 (2H); 4.2–4.5 (1H); 5.0–5.4 (2H); 7.1 (1H); 7.2 (1H); 11.8 (1H)

f) Preparation of 1-cyclohexyl-6-trifluoromethoxy-7-(1-pyrrolyl)-2,3(1H,4H)-quinoxalinedione A solution of 2.4 g (7.3 mmol) of 1-cyclohexyl-6-trifluoromethyl-7-amino-2,3(1H,4H)-quinoxalinedione and 1 g (7.3 mmol) of 2,5-dimethoxytetrahydrofuran in 100 ml of glacial acetic acid was refluxed for 30 minutes. The reaction mixture was then poured into ice-water. The resulting product was filtered off with suction.

Yield: 69%

Melting point >320° C.

$^1$H-NMR (D$_6$-DMSO): δ (ppm): 1.15 (1H); 1.45 (2H); 1.6 (1H); 1.7 (2H); 1.75 (2H); 2.4 (2H); 4.4 (1H); 6.2 (2H); 6.9 (2H); 7.55 (1H); 7.6 (1H)

EXAMPLE 4

1-Cyclohexyl-6-trifluoromethyl-7-(2-methoxycarbonyl-1-pyrrolyl)-2,3(1H,4H)-quinoxalinedione In place of 2,5-dimethoxytetrahydrofuran, 1.2 g (6.1 mmol) of 2-methoxycarbonyl-2,5-dimethoxytetrahydrofuran were dissolved with 2 g (6.1 mmol) of 1-cyclohexyl-6-trifluoromethyl-7-amino-2,3(1H, 4H)-quinoxalinedione in 100 ml of acetic acid and refluxed for 30 minutes. The mixture was then worked up as in Example 3f.

Yield: 61%

Melting point 200° C.

$^1$H-NMR (D$_6$-DMSO): δ (ppm): 1.2–1.4 (m, 2H); 1.7–2.0 (m, 6H); 2.4–2.6 (m,2H); 3.7 (s,3H); 4.2–4.3 (m,1H); 6.4 (dd,1H); 6.95 (m,1H); 7.15 (dd,1H); 7.3 (1H); 7.6 (1H)

EXAMPLE 5

6-(2-Methoxycarbonyl-1-pyrrolyl)-7-nitro-2,3(1H, 4H)-quinoxalinedione a) Preparation of 6-trifluoroacetamido-2,3(1H,4H)-quinoxalinedione A solution of 28 g (0.16 mol) of 6-amino-2,3(1H,4H)-quinoxalinedione in 200 ml of trifluoroacetic acid was refluxed with 35.7 g (0.17 mol) of trifluoroacetic anhydride for one hour. The reaction mixture was cooled, and the crude product was filtered off and worked up by conventional methods.

Yield: 83%

Melting point >330° C.

$^1$H-NMR (D$_6$-DMSO): δ (ppm): 7.1 (1H); 7.3 (1H); 7.6 (1H); 11.3 (1H); 12.1 (1H)

b) Preparation of 6-trifluoroacetamido-7-nitro-2,3(1H,4H)-quinoxalinedione

A solution of 39 g (0.14 mol) of 6-trifluoroacetamido-2, 3(1H,4H)-quinoxalinedione in 500 ml of concentrated sulfuric acid was cooled to 0° C., 12.1 g (0.14 mol) of sodium nitrate were added a little at a time, and the mixture was stirred at room temperature for 30 minutes. It was then poured into ice-water, and the crude product was filtered off and worked up by conventional methods.

Yield: 94%
Melting point >320° C.
$^1$H-NMR (D$_6$-DMSO): δ (ppm): 7.3 (1H); 7.8 (1H); 11.6 (1H); 12.2 (1H); 12.4 (1H)

c) Preparation of 6-amino-7-nitro-2,3(1H,4H)-quinoxalinedione

A solution of 41 g (0.13 mol) of 6-trifluoroacetamido-7-nitro-2,3(1H,4H)-quinoxalinedione in 300 ml of ethanol and 700 ml of 3 molar hydrochloric acid was refluxed for 3 hours. The reaction mixture was cooled, and the crude product was filtered off and worked up by conventional methods.

Yield: 84%
Melting point >330° C.
$^1$H-NMR (D$_6$-DMSO): δ (ppm): 6.6 (1H); 7.2–7.6 (3H); 7.8 (1H); 11.7 (1H); 12.1 (1H)

d) Preparation of 6-(2-methoxycarbonyl-1-pyrrolyl)-7-nitro-2,3(1H,4H)-quinoxalinedione 7 g (27.1 mmol) of 6-amino-7-nitro-2,3(1H,4H)-quinoxalinedione, 5.1 g (27.1 mmol) of 2-methoxycarbonyl-2,5-dimethoxytetrahydrofuran and 4.5 g (54.2 mmol) of sodium acetate in 500 ml of glacial acetic acid were refluxed for one hour. The reaction mixture was concentrated and then the crude product was purified by column chromatography on silica gel (mobile phase: toluene/acetone/glacial acetic acid=10/10/1).

Yield: 59%
Melting point >310° C.
$^1$H-NMR (D$_6$-DMSO): δ (ppm): 3.6 (s,3H); 6.4 (dd,1H); 7.05 (m,2H); 7.3 (dd,1H); 7.95 (s,1H); 12.4 (m,2H)

EXAMPLE 6

6-(2,5-Dimethyl-1-pyrrolyl)-7-nitro-2,3(1H,4H)-quinoxalinedione 13.5 mmol of 6-amino-7-nitro-2,3(1H,4H)-quinoxalinedione were reacted with 13.5 mmol of 2,5-dimethyl-2,5-dimethoxytetrahydrofuran by the method of Example 5d.

Yield: 42%
Melting point >320° C.
$^1$H-NMR (D$_6$-DMSO): δ (ppm): 1.9 (6H); 5.8 (2H); 7.0 (1H); 7.9 (1H); 12 (2H)

EXAMPLE 7

6-(1-Pyrrolyl)-7-nitro-2,3(1H,4H)-quinoxalinedione 23.2 mmol of 6-amino-7-nitro-2,3(1H,4H)-quinoxalinedione were reacted with 23.2 mmol of 2,5-dimethoxytetrahydrofuran by the method of Example 5d.

Yield: 66%
Melting point >310° C.
$^1$H-NMR (D$_6$-DMSO): δ (ppm): 6.2 (2H); 6.8 (2H); 7.1 (1H); 7.8 (1H); 12.5 (2H)

EXAMPLE 8

6-(1-Pyrrolyl)-7-trifluoromethyl-2,3(1H,4H)-quinoxalinedione 12.2 mmol of 6-amino-7-trifluoromethyl-2,3(1H,4H)-quinoxalinedione were reacted with 12.2 mmol of 2,5-dimethoxytetrahydrofuran by the method of Example 5d.

Yield: 49%
Melting point >300° C.
$^1$H-NMR (D$_6$-DMSO): δ (ppm): 6.2 (2H); 6.9 (2H); 7.0 (1H); 7.5 (1H); 12.5 (2H)

EXAMPLE 9

6-(2-Methoxycarbonyl-1-pyrrolyl)-7-trifluoromethyl-2,3(1H,4H)-quinoxalinedione 51 mmol of 6-amino-7-trifluoromethyl-2,3(1H,4H)-quinoxalinedione were reacted with 51 mmol of 2-methoxycarbonyl-2,5-dimethoxytetrahydrofuran by the method of Example 5d.

Yield: 86%
Melting point >310° C.
$^1$H-NMR (D$_6$-DMSO): δ (ppm): 3.6 (3H); 6.3 (1H); 7.0 (2H); 7.1 (1H); 7.5 (1H); 12.5 (2H)

EXAMPLE 10

6-(2-Carboxyl-1-pyrrolyl)-7-trifluoromethyl-2,3(1H,4H)-quinoxalinedione 13 g (36.8 mmol) of 6-(2-methoxycarbonyl-1-pyrrolyl)-7-trifluoromethyl-2,3(1H,4H)-quinoxalinedione were mixed with 75 ml of 2 molar sodium hydroxide solution and stirred at room temperature for 16 hours. The mixture was neutralized with 2 molar hydrochloric acid and then extracted with methylene chloride and worked up in a conventional way.

Yield: 79%
Melting point >320° C.
$^1$H-NMR (D$_6$-DMSO): δ (ppm): 6.3 (1H); 6.95 (1H); 7.0 (1H); 7.1 (1H); 7.5 (1H); 12.0 (2H)

EXAMPLE 11

6-(2,5-Dimethyl-1-pyrrolyl)-7-trifluoromethyl-2,3(1H,4H)-quinoxalinedione 12.2 mmol of 6-amino-7-trifluoromethyl-2,3(1H,4H)-quinoxalinedione were reacted with 12.2 mmol of 2,5-dimethyl-2,5-dimethoxytetrahydrofuran by the method of Example 5d.

Yield: 54%
Melting point >350° C.
$^1$H-NMR (D$_6$-DMSO): δ (ppm): 1.9 (6H); 5.8 (2H); 6.9 (1H); 7.6 (1H); 12.5 (2H)

EXAMPLE 12

6-(2,5-Dimethyl-1-pyrrolyl)-7-chloro-2,3(1H,4H)-quinoxalinedione 14.2 mmol of 6-ammonio-7-chloro-2,3(1H,4H)-quinoxalinedione chloride were reacted with 14.2 mmol of 2,5-dimethyl-2,5-dimethoxytetrahydrofuran by the method of Example 5d.

Yield: 57%
Melting point >300° C.
$^1$H-NMR (D$_6$-DMSO): δ (ppm): 1.9 (6H); 5.8 (2H); 7.0 (1H); 7.3 (1H); 12.0 (2H)

EXAMPLE 13

6-(2,5-Diphenyl-1-pyrrolyl)-7-chloro-2,3(1H,4H)-quinoxalinedione 16.5 mmol of 6-ammonio-7-chloro-2,3(1H,4H)-quinoxalinedione chloride were reacted with 16.5 mmol of 2,5-diphenyl-2,5-dimethoxytetrahydrofuran by the method of Example 5d.

Yield: 13%

Melting point >230° C.
$^1$H-NMR (D$_6$-DMSO): δ (ppm): 6.5 (2H); 7.2 (1H); 12.0 (2H)

EXAMPLE 14

6-(3-Formyl-1-pyrrolyl)-7-chloro-2,3(1H,4H)-quinoxalinedione 16.5 mmol of 6-ammonio-7-chloro-2,3(1H,4H)-quinoxalinedione chloride were reacted with 16.5 mmol of 3-formyl-2,5-dimethoxytetrahydrofuran by the method of Example 5d.
Yield: 77%
Melting point >300° C.
$^1$H-NMR (D$_6$-DMSO): δ (ppm): 6.6 (s,1H); 7.15 (s,1H); 7.2 (s,1H); 7.3 (s,1H); 7.9 (s,1H); 9.8 (s,1H); 12.5 (m,2H)

EXAMPLE 15

6-(3-Propionyl-1-pyrrolyl)-7-chloro-2,3(1H,4H)-quinoxalinedione 14.2 mmol of 6-ammonio-7-chloro-2,3(1H,4H)-quinoxalinedione chloride were reacted with 14.2 mmol of 3-propionyl-2,5-dimethoxytetrahydrofuran by the method of Example 5d.
Yield: 69%
Melting point >300° C.
$^1$H-NMR (D$_6$-DMSO): δ (ppm): 1.05 (t,3H); 2.7 (q,2H); 6.6 (dd,1H); 7.0 (dd,1H); 7.1 (s,1H); 7.25 (s,1H); 7.8 (m,1H); 12.0 (2H)

EXAMPLE 16

6-(2-Methoxy-1-pyrrolyl)-2,3(1H,4H)-quinoxalinedione 28 mmol of 6-amino-2,3(1H,4H)-quinoxalinedione were reacted with 28 mmol of 2,2,5-trimethoxytetrahydrofuran by the method of Example 5d.
Yield: 97%
Melting point >310° C.
$^1$H-NMR (D$_6$-DMSO): δ (ppm): 3.6 (3H); 6.3 (1H); 7.0 (2H); 7.1 (1H); 7.2 (2H); 12.0 (2H)

EXAMPLE 17

5-(1-Pyrrolyl)-7-trifluoromethyl-2,3(1H,4H)-quinoxalinedione 12.2 mmol of 5-amino-7-trifluoromethyl-2,3(1H,4H)-quinoxalinedione were reacted with 12.2 mmol of 2,5-dimethoxytetrahydrofuran by the method of Example 5d.
Yield: 48%
Melting point >320° C.
$^1$H-NMR (D$_6$-DMSO): δ (ppm): 6.3 (2H); 7.0 (2H); 7.4 (1H); 7.7 (1H); 11.3 (1H); 12.2 (1H)

EXAMPLE 18

9-(2-Methoxycarbonyl-1-pyrrolyl)benzo[f]quinoxaline-2,3(1H,4H)-dione 8.8 mmol of 9-aminobenzo[f]quinoxaline-2,3(1H,4H)-dione were reacted with 8.8 mmol of 2-methoxycarbonyl-2,5-dimethoxytetrahydrofuran by the method of Example 5d.
Yield: 58%
Melting point >300° C.
$^1$H-NMR (D$_6$-DMSO): δ (ppm): 3.5 (3H); 6.5 (1H); 7.0 (1H); 7.1 (1H); 7.3 (2H); 7.5 (1H); 7.6 (1H); 8.6 (1H); 12.5 (2H)

EXAMPLE 19

9-(2,5-Dimethyl-1-pyrrolyl)benzo[f]quinoxaline-2,3(1H,4H)-dione 8.8 mmol of 9-aminobenzo[f]quinoxaline-2,3(1H,4H)-dione were reacted with 8.8 mmol of 2,5-dimethyl-2,5-dimethoxytetrahydrofuran by the method of Example 5d.
Yield: 27%
Melting point >320° C.
$^1$H-NMR (D$_6$-DMSO): δ (ppm): 1.8 (6H); 5.95 (2H); 6.95 (1H); 7.3 (1H); 7.5 (1H); 7.7 (1H); 8.7 (1H); 12.5 (2H)

EXAMPLE 20

9-(1-Pyrrolyl)benzo[f]quinoxaline-2,3(1H,4H)-dione 8.8 mmol of 9-ammoniobenzo[f]quinoxaline-2,3(1H,4H)-dione chloride were reacted with 8.8 mmol of 2,5-dimethoxytetrahydrofuran by the method of Example 5d.
Yield: 62%
Melting point >300° C.
$^1$H-NMR (D$_6$-DMSO): δ (ppm): 6.3 (2H); 7.0 (2H); 7.3 (1H); 7.5 (2H); 7.7 (1H); 8.7 (1H); 12.5 (2H)

EXAMPLE 21

7,8(6H,9H)-Dioxopyrazino[5,6-g]pyrrolo[1,2-c]quinoxalin-2(4H)-one

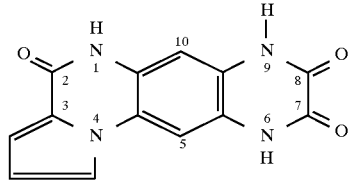

A solution of 4.8 g (14.5 mmol) of 6-(2-methoxycarbonyl-1-pyrrolyl)-7-nitro-2,3(1H,4H)-quinoxalinedione in 250 ml of glacial acetic acid was heated to 80° C., 8 g (145.3 mmol) of iron powder were added a little at a time, and the mixture was refluxed for 2 hours. The reaction mixture was concentrated and then dilute hydrochloric acid was added to the crude product. The product was filtered off and dried.
Yield: 72%
Melting point >320° C.
$^1$H-NMR (D$_6$-DMSO): δ (ppm): 6.7 (1H); 7.1 (1H); 7.4 (1H); 7.6 (1H); 7.9 (1H); 11.3 (1H); 12.0–12.2 (2H)

EXAMPLE 22

6-Chloro-7-(2-methoxycarbonyl-1-pyrrolyl)-2,3(1H,4H)-quinoxalinedione 10 g (47.25 mmol) of 7-amino-6-chloro-2,3(1H,4H)-quinoxalinedione and 8.9 g (47.25 mmol) of 2-methoxycarbonyl-2,5-dimethoxytetrahydrofuran in 150 ml of acetic acid were refluxed for 2 h. The precipitate was then filtered off with suction to yield 6.6 g (44%) of the product. Melting point >260° C.

$^1$H-NMR (D$_6$-DMSO): δ =3.6 (3H); 6.35 (1H); 7.0 (1H); 7.1 (1H); 7.15 (1H); 7.25 (1H) and 12.1 (broad, 2H) ppm.

EXAMPLE 23

1-(Methoxycarbonylmethyl)-7-(2,5-dimethyl-1-pyrrolyl)-6-trifluoromethyl-2,3 (1H,4H)-quinoxalinedione 2.2 g (6.8 mmol) of 6-(2,5-dimethyl-1-pyrrolyl)-7-trifluoromethyl-2,3(1H,4H)-quinoxalinedione (Example 11) were dissolved in 25 ml of anhydrous dimethylformamide under nitrogen and 0.245 g (8.2 mmol) of 80% sodium hydride was added a little at a time. The mixture was stirred at room temperature for 1 hour and then the solution was cooled to −25° C., and 1.4 g (8.9 mmol) of ethyl bromoacetate dissolved in 3 ml of dimethylformamide were added dropwise. The mixture was stirred for 90 minutes and then poured onto ice, acidified with dilute hydrochloric acid and extracted with ethyl acetate. The organic phase was dried and evaporated in a rotary evaporator. The residue was purified by chromatography on silica gel (mobile phase: n-heptane/ethyl acetate=2/1), resulting in 0.8 g (30%) of the product.

Melting point >220° C. (decomposition)

$^1$H-NMR (CDCl$_3$): δ=1.85 (6H); 3.65 (3H); 5.1 (2H); 5.8 (2H); 7.4 (1H) and 7.7 (1H) ppm.

EXAMPLE 24

1-(Methoxycarbonylmethyl)-7-(1-pyrrolyl)-6-trifluoromethyl-2,3(1H,4H)-quinoxalinedione 35 g (118.6 mmol) of 6-(1-pyrrolyl)-7-trifluoromethyl-2,3(1H,4H)-quinoxalinedione (Example 2) were reacted with 23.8 g (155.5 mmol) of methyl bromoacetate as in Example 23. The mobile phase used for the chromatography was methylene chloride/ethyl acetate =3/2. 17.3 g (40%) of the product were obtained.

Melting point 141°–142° C.

$^1$H-NMR (D$_6$-DMSO): δ =3.7 (3H); 5.0 (2H); 6.2 (2H); 6.85 (2H); 7.6 (1H); 7.65 (1H) and 12.5 (broad) ppm.

EXAMPLE 25

1-(Carboxymethyl)-7-(1-pyrrolyl)-6-trifluoromethyl-2,3(1H,4H)-quinoxalinedione 2 g (5.45 mmol) of 1-(methoxycarbonylmethyl)-7-(1-pyrrolyl)-6-trifluoromethyl-2,3(1H,4H)-quinoxalinedione (Example 24) were dissolved in 30 ml of tetrahydrofuran, and 0.4 g (16.4 mmol) of lithium hydroxide dissolved in 4 ml of water was added. The mixture was stirred at room temperature for 16 h and then organic solvent was removed under reduced pressure. The aqueous phase was acidified with 1M hydrochloric acid and extracted with ethyl acetate. The organic phase was dried and concentrated under reduced pressure. The residue was recrystallized from methanol, resulting in 1.3 g (69%) of the product. Melting point 161°–163° C. (decomposition).

$^1$H-NMR (D$_6$-DMSO): δ=4.95 (2H); 5.0 (2H); 6.2 (2H); 6.9 (2H); 7.5 (1H); 7.6 (1H) and 11.5 (broad) ppm.

EXAMPLE 26

1-Methylcarbamoylmethyl-7-(1-pyrrolyl)-6-trifluromethyl-2,3(1H,4H)-quinoxalinedione 3 g (8.2 mmol) of 1-(methoxycarbonylmethyl)-7-(1-pyrrolyl)-6-trifluoromethyl-2,3(1H,4H)-quinoxalinedione were dissolved in 100 ml of approx. 5M methanolic ammonia solution and stirred at room temperature for 2 h. The mixture was then concentrated under reduced pressure, and the residue was purified by chromatography on silica gel (mobile phase: methylene chloride/methanol/tetrahydrofuran=4:2:1) to yield 1.8 g (63%) of the product. Melting point >250° C.

$^1$H-NMR (D$_6$-DMSO): δ=2.3 (3H); 4.4 (2H); 6.2 (2H); 6.85 (2H); 7.0 (1H) and 7.5 (1H) ppm.

EXAMPLE 27

1-Benzylcarbamoylmethyl-7-(1-pyrrolyl)-6-trifluoromethyl-2,3(1H,4H)-quinoxalinedione 2.0 g (6.5 mmol) of 1-carboxymethyl-7-(1-pyrrolyl)-6-trifluoromethyl-2,3(1H,4H)-quinoxalinedione and 0.64 g (5.9 mmol) of benzylamine were dissolved in 50 ml of anhydrous dimethylformamide. At 0° C., 1.6 g (5.9 mmol) of diphenylphosphoryl azide dissolved in a little dimethylformamide, and 1.3 g (12.5 mmol) of triethylamine were successively added dropwise. The mixture was stirred at room temperature for 4 h and then poured into water buffered with sodium bicarbonate. The resulting precipitate was filtered off with suction to yield 1.6 g (62%) of the product. Melting point 241°–242° C.

$^1$H-NMR (D$_6$-DMSO): δ=4.3 (2H); 6.3 (1H); 6.9 (1H); 7.0 (1H); 7.05 (1H); 7.1–7.4 (6H) and 8.7 (1H) ppm.

EXAMPLE 28

1–Cyclohexyl-7-nitro-6-(1-pyrrolyl)-2,3(1H,4H)-quinoxalinedione a) N-Cyclohexyl-2,4-dinitroaniline 50 g (0.247 mol) of 1-chloro-2,4-dinitrobenzene, 73.5 g (0.74 mol) of cyclohexylamine, 68 g (0.5 mol) of potassium carbonate and 20 ml of water were heated in 400 ml of dimethylformamide at 80°–90° C. for 3 h. The mixture was then concentrated under reduced pressure, and the residue was partitioned between water and ethyl acetate. The organic phase was dried and concentrated under reduced pressure to yield 63.9 g (98%) of the product. Melting point 155° C.

$^1$H-NMR (D$_6$-DMSO): δ=1.2–2.1 (10H); 3.8 (1H); 7.3 (1H); 8.2 (1H); 8.5 (NH) and 8.9 (1H) ppm.

b) N-Cyclohexyl-2,4-diaminoaniline 60.0 g (0.23 mol) of N-cyclohexyl-2,4-dinitroaniline were dissolved in 500 ml of tetrahydrofuran and, after addition of 3 g of palladium/carbon (10%), were hydrogenated. The mixture was then filtered and the filtrate was concentrated under reduced pressure to yield 47.2 g (100%) of the product.

$^1$H-NMR (D$_6$-DMSO): δ=1.0–2.0 (10H); 2.8 (1H); 4.0—4.0 (3H,NH); 5.75 (1H); 5.9 (1H) and 6.2 (1H) ppm.

c) Ethyl N-(1-cyclohexyl-2,3(1H,4H)-quinoxalinedion-6-yl) oxamate 46 g (0.224 mol) of N-cyclohexyl-2,4-diaminoaniline were refluxed in 500 ml of diethyl oxalate for 2 h. After cooling, ether was added, and the precipitate was filtered off with suction to yield 48.3 g (60%) of the product.

Melting point 271°–272° C. (decomposition).

$^1$H-NMR (D$_6$-DMSO): δ=1.3 (3H); 1.3–2.0 (8H); 2.3–2.5 (2H); 4.4 (2H); 4.5 (1H); 7.5 (1H); 7.6 (1H); 7.8 (1H); 10.9 (1H) and 12.1 (1H) ppm.

d) Ethyl N-(1-cyclohexyl-7-nitro-2,3(1H,4H)-quinoxalinedion-6-yl)oxamate 48 g (0.133 mol) of ethyl N-(1-cyclohexyl-2,3(1H,4H)-quinoxalinedion-6-yl)oxamate were dissolved in 1 l of concentrated sulfuric acid and, at 0° C., 11.35 g (0.133 mol) of sodium nitrate were added a little at a time. The mixture was stirred at 0° C. for a further 2 h and poured into a large quantity of ice. The precipitate was filtered off with suction to yield 50.1 g (93%) of the product.

Melting point 260° C.

$^1$H-NMR (D$_6$-DMSO): δ=1.4–2.0 (11H); 2.3 (2H); 4.3 (2H); 4.5 (1H); 8.1 (1H); 8.2 (1H); 11.5 (1H) and 12.5 (1H) ppm.

e) 6-Amino-1-cyclohexyl-7-nitro-2,3(1H,4H)-quinoxalinedione 42 g (0.1 mol) of ethyl N-(1-cyclohexyl-7-nitro-2,3(1H,4H)-quinoxalinedion-6-yl)oxamate were refluxed in a mixture of 1 l of concentrated sulfuric acid and 500 ml of ethanol for 4 h. The precipitate was filtered off with suction to yield 34 g (100%) of the product. Melting point >250° C. (decomposition).

$^1$H-NMR (D$_6$-DMSO): δ=1.1–2.0 (8H); 2.3 (2H); 4.4 (1H); 6.7 (1H); 7.0–7.5 (2H, broad, NH$_2$); 8.0 (1H) and 12.2 (1H) ppm.

f) 1-Cyclohexyl-7-nitro-6-(1-pyrrolyl)-2,3(1H,4H)-quinoxalinedione 3.0 g (99 mmol) of 6-amino-1-cyclohexyl-7-nitro-2,3(1H,4H)-quinoxalinedione and 1.3 g (99 mmol) of 2,5-dimethoxytetrahydrofuran were refluxed in 70 ml of acetic acid for 30 minutes. The mixture was then diluted with water, and the precipitate was filtered off with suction to yield 2.4 g (69%) of the product. Melting point 197° C.

$^1$H-NMR (D$_6$-DMSO): δ=1.1–2.0 (8H); 2.3 (2H); 4.5 (1H); 6.3 (2H); 6.9 (2H); 7.2 (1H); 8.2 (1H) and 12.4 (1H) ppm.

EXAMPLE 29

1-Cyclohexyl-6-(2-methoxycarbonyl-1-pyrrolyl)-7-nitro-2,3(1H,4H)-quinoxalinedione 10 g (33 mmol) of 6-amino-1-cyclohexyl-7-nitro-2,3(1H,4H)-quinoxalinedione (Example 28e), 6.9 g (36 mmol) of 2-methoxycarbonyl-2,5-dimethoxytetrahydrofuran and a spatula tip of p-toluenesulfonic acid were refluxed in a mixture of 50 ml of dimethylformamide and 50 ml of toluene with a water trap. After reaction was complete, the mixture was concentrated under reduced pressure, and the residue was treated with water. The precipitate was filtered off with suction to yield 11 g (79%) of the product. Melting point 211°–212° C.

$^1$H-NMR (D$_6$-DMSO): δ=1.2–2.0 (8H); 2.4 (2H); 3.6 (3H); 4.5 (1H); 6.4 (1H); 7.05 (1H); 7.3 (1H); 8.0 (1H); 8.3 (1H) and 12.5 (1H) ppm.

EXAMPLE 30

1-Ethyl-7-nitro-6-(1-pyrrolyl)-2,3(1H,4H)-quinoxalinedione a) 6-Amino-1-ethyl-7-nitro-2,3(1H,4H)-quinoxalinedione Ethyl N-(1-ethyl-7-nitro-2,3(1H,4H)-quinoxalinedion-6-yl)oxamate was prepared as in Example 28a–d from 1-chloro-2,4-dinitrobenzene and ethylamine.

24 g (68.6 mmol) of this amide were refluxed in a mixture of 13 ml of concentrated sulfuric acid, 240 ml of water and 250 ml of ethanol for 3 h. The precipitate was then filtered off with suction to yield 16.2 g (98%) of the product.

$^1$H-NMR (D$_6$-DMSO): δ=1.2 (3H); 4.1 (2H); 6.7 (1H); 7.2–7.6 (2H, NH$_2$); 7.8 (1H) and 12.2 (1H) ppm.

b) 1-Ethyl-7-nitro-6-(1-pyrrolyl)-2,3(1H,4H)-quinoxalinedione 4.0 g (16 mmol) of 6-amino-1-ethyl-7-nitro-2,3(1H,4H)-quinoxalinedione, 2.4 g (18 mmol) of 2,5-dimethoxytetrahydrofuran and a spatula tip of p-toluenesulfonic acid were refluxed in a mixture of 50 ml of dimethylformamide and 50 ml of toluene with a water trap for 3 h. The mixture was then concentrated under reduced pressure, and the residue was treated with methanol. The precipitate was filtered off with suction to yield 18 g (3%) of the product.

Melting point 248°–250° C.

$^1$H-NMR (D$_6$-DMSO): δ=1.2 (3H); 4.2 (2H); 6.2 (2H); 6.9 (2H); 7.2 (1H); 8.0 (1H) and 12.4 (1H) ppm.

EXAMPLE 31

9-(2,5-Dimethyl-1-pyrrolyl)-1-(ethoxycarbonylmethyl)-benzo[f]quinoxaline-2,3(1H,4H)-dione a) 2-Methoxy-1-nitronaphthalene 100 g (0.63 mol) of 2-methoxynaphthalene were dissolved in 1.2 l of acetic acid and, at 10° C., 100 ml of 65% strength nitric acid were slowly added dropwise. The mixture was stirred at 10° C. for a further 2 h. The precipitate was then filtered off with suction to yield 72.5 g (57%). Melting point 129°–130° C.

$^1$H-NMR (D$_6$-DMSO): δ=4.1 (3H); 7.5–7.8 (4H); 8.05 (1H) and 8.2 (1H) ppm.

b) N-(1-Nitro-2-naphthyl)aminoacetic acid 50 g (0.246 mol) of the product 31a, 100 g (1.3 mol) of glycine and 100 g (0.7 mol) of potassium carbonate in 400 ml of diethylene glycol were heated at 140° C. for 10 min. The mixture was then immediately poured into ice-water, acidified with concentrated hydrochloric acid and extracted with 1.5 l of ethyl acetate. The resulting precipitate was filtered off with suction to yield 29.6 g (49%) of the product. Melting point >155° C. (decomposition).

$^1$H-NMR (D$_6$-DMSO): δ=4.3 (2H); 7.2 (1H); 7.35 (1H); 7.6 (1H); 7.8 (1H); 8.0 (1H); 8.4 (1H); 8.7 (1H,NH) and about 12 (broad) ppm.

c) N-(1-Amino-2-naphthyl)aminoacetic acid 28 g (0.11 mol) of the product 31b were dissolved in 300 ml of ethanol and, after addition of 10 ml of acetic acid and 2 g of palladium/carbon (10%), hydrogenated under 1 bar at room temperature. The mixture was then filtered, and the filtrate was concentrated under reduced pressure to yield 23.9 g (98%) of the product.

$^1$H-NMR (D$_6$-DMSO): δ=3.8 (2H); 6.2 (NH); 7.1 (1H); 7.2 (1H); 7.3–7.5 (2H); 7.7 (1H); 8.1 (1H) and 10.5 (1H, CO$_2$H) ppm.

d) 1-Carboxymethylbenzo[f]quinoxaline-2,3(1H,4H)-dione 22 g (0.1 mol) of the product 31c and 28 ml (0.2 mol) of triethylamine were dissolved in 300 ml of anhydrous tetrahydrofuran. Then, at 0° to 5° C., 12.5 ml (0.11 mol) of ethyl oxalyl chloride dissolved in 50 ml of anhydrous tetrahydrofuran were added dropwise. The mixture was stirred at 0° to 5° C. for 1 h and then concentrated under reduced pressure, and the residue was partitioned between ethyl acetate and water. The organic phase was dried and concentrated under reduced pressure. This residue was refluxed in a mixture of 50 ml of ethanol and 200 ml of concentrated hydrochloric acid for 1.5 h. The mixture was then poured into ice-water, and the precipitate was filtered off with suction to yield 16.8 g (61%) of the product. Melting point 288°–291° C. (decomposition).

$^1$H-NMR (D$_6$-DMSO): δ=5.0 (2H); 7.4–7.6 (3H); 7.7 (1H); 7.9 (1H); 8.6 (1H); 12.3 (l1H) and about 13 (broad) ppm.

e) 1-Ethoxycarbonylmethylbenzo[f]quinoxaline-2,3(1H,4H)-dione 17 g (62.9 mmol) of the product 31d were stirred in a mixture of 250 ml of concentrated sulfuric acid and 70 ml of ethanol at 55° C. for 3 h. The mixture was then poured into ice-water, and the precipitate was filtered off with suction to yield 18.3 g (98%) of the product.

Melting point >250° C.

$^1$H-NMR (D$_6$-DMSO): δ=1.2 (3H); 4.2 (2H); 5.1 (2H); 7.3–7.6 (4H); 7.85 (1H) and 8.7 (1H) ppm.

f) 1-Ethoxycarbonylmethyl-9-nitrobenzo[f]quinoxaline-2,3(1H,4H)-dione 18 g (60.3 mmol) of the product 31e were suspended in 200 ml of acetic acid and, at room temperature, 50 ml of 65% strength nitric acid were cautiously added. The mixture was then heated to 80° C. After the reaction was complete (solution changed color from dark to pale red), the mixture was poured into ice, and the precipitate was filtered off with suction to yield 16.9 g (82%) of the product. Melting point >250° C.

$^1$H-NMR (D$_6$-DMSO): δ=1.3 (3H); 4.2 (2H); 5.2 (2H); 7.7 (2H); 8.3–8.4 (2H); 8.8 (1H) and 12.7 (1H) ppm.

g) 9-Amino-1-ethoxycarbonylmethylbenzo[f]quinoxaline-2,3(1H,4H)-dione 16.5 g (48 mmol) of the product 31f were dissolved in 150 ml of dimethylformamide and, after addition of 1.5 g of palladium/carbon (10%), hydrogenated under 1 bar at room temperature. The mixture was then filtered, and the filtrate was concentrated under reduced pressure to yield 13.1 g (88%) of the product.

Melting point >250° C.

$^1$H-NMR (D$_6$-DMSO): δ=1.2 (3H); 4.2 (2H); 5.0 (2H); 5.7–6.0 (2H, NH, broad); 6.6 (1H); 7.4 (1H); 7.5 (1H); 8.2 (1H); 8.5 (1H) and 12.0 (1H) ppm.

h) 9-(2,5-Dimethyl-1-pyrrolyl)-1-ethoxycarbonylmethylbenzo[f]quinoxaline-2,3(1H,4H)-dione 12.5 g (40 mmol) of the product 31g and 4.7 ml (40 mmol) of 2,5-hexanedione were refluxed in 130 ml of acetic acid for 15 minutes. The mixture was then concentrated under reduced pressure, and the residue was dispersed in a little ethanol and filtered off with suction to yield 10.0 g (65%) of the product.

$^1$-NMR (D$_6$-DMSO): δ=1.2 (3H); 1.8 (6H); 4.15 (2H); 5.2 (2H); 5.9 (2H); 6.9 (1H); 7.55 (1H); 7.7 (1H); 7.75 (1H); 8.75 (1H); 12.0 (broad, 1H) and 12.5 (1H) ppm.

EXAMPLE 32

1-Ethyl-6-nitro-7-(1-pyrrolyl)-2,3(1H,4H)-quinoxalinedione a) 1-Ethyl-7-nitro-2,3(1H,4H)-quinoxalinedione 14.2 g (57 mmol) of 6-amino-1-ethyl-7-nitro-2,3(1H,4H)-quinoxalinedione (Example 30 a) were suspended in 340 ml of acetic acid. To this was added dropwise at 10°–20° C. a solution of 5.1 g (74 mmol) of sodium nitrite and 80 ml of concentrated sulfuric acid. The mixture was stirred for a further 30 minutes and then this solution was added dropwise to another suspension of 16.3 g (114 mmol) of copper (I) oxide in 140 ml ethanol. The mixture was stirred for a further 10 minutes and then poured into 1 l of ice-water. After filtration, the filtrate was extracted with methylene chloride and the organic phase was dried and concentrated under reduced pressure to yield 8.5 g (64%) of the product.

Melting point >300° C.

$^1$H-NMR (D$_6$-DMSO): δ=1.2 (3H); 4.2 (2H); 7.3 (1H); 8.1 (2H) and 12.5 (1H) ppm.

b) 7-Amino-1-ethyl-2,3(1H,4H)-quinoxalinedione 8.3 g (35 mmol) of 1-ethyl-6-nitro-2,3 (1H,4H)-quinoxalinedione were dissolved in 300 ml of dimethylformamide and, after addition of 2 g of palladium/carbon (10%), were hydrogenated. The mixture was then filtered and the filtrate was concentrated under reduced pressure to yield 5.9 g (81%) of the product.

Melting point 271°–273° C. (decomposition).

$^1$H-NMR (D$_6$-DMSO): δ=1.2 (3H); about 3.3 (broad, 1H); 4.05 (2H); 6.4 (1H); 6.6 (1H); 6.9 (1H) and about 11.7 (broad) ppm.

c) 7-Acetamido-1-ethyl-2,3(1H,4H)-quinoxalinedione 5.5 g (27 mmol) of 7-amino-1-ethyl-2,3(1H,4H)-quinoxalinedione were refluxed in 75 ml of acetic anhydride for 1 h. The mixture was then poured into ice-water and filtered. The filtrate was concentrated under reduced pressure to yield 5.7 g (86%) of the product. Melting point 303°–304° C. (decomposition).

$^1$H-NMR (D$_6$-DMSO): δ=1.2 (3H); 4.0 (2H); 7.0 (1H); 7.3 (1H); 7.7 (1H); 10.0 (1H) and about 12 (broad) ppm.

d) 7-Amino-1-ethyl-6-nitro-2,3(1H,4H)-quinoxalinedione 5.2 g (21 mmol) of 7-acetamido-1-ethyl-2,3(1H,4H)-quinoxalinedione were dissolved in 75 ml of concentrated sulfuric acid and, at 0°–5° C., 2 g (23 mmol,) of sodium nitrate were added. The mixture was stirred at 0°–5° C. for 2 h and then poured into ice-water and stirred at room temperature for 16 h. The mixture was then neutralized with dilute sodium hydroxide solution and sodium bicarbonate solution and concentrated under reduced pressure. The residue was extracted with dimethylformamide and then the organic phase was concentrated anew. The residue was purified on silica gel (mobile phase: toluene/acetone/acetic acid=10:10:1) to yield 1.2 g (23%) of the product.

$^1$H-NMR (D$_6$-DMSO): δ=1.2 (3H); 4.0 (2H); 6.9 (1H); 7.3 (2H); 7.7 (1H) and about 12 (broad) ppm.

e) 1-Ethyl-6-nitro-7-(1-pyrrolyl)-2,3(1H,4H)-quinoxalinedione 0.9 g (3.5 mmol) of 7-amino-1-ethyl-6-nitro-2,3(1H,4H)-quinoxalinedione and 0.58 g (4.4 mmol) of 2,5-dimethoxytetrahydrofuran in 20 ml of acetic acid were refluxed for 2 h. The mixture was then concentrated under reduced pressure, and the residue was purified by chromatography on silica gel (mobile phase: toluene/acetone/acetic acid=10:10:1) to yield 0.7 g (68%) of the product. Melting point >300° C.

$^1$H-NMR (D$_6$-DMSO): δ=1.2 (3H); 4.2 (2H); 6.3 (1H); 6.9 (2H); 7.5 (1H); 7.8 (1H) and about 12.5 (broad) ppm.

EXAMPLE 33

9-(2,3-Dimethyl-1-pyrrolyl)-4-(ethoxycarbonylmethyl-benzo[f]quinoxaline-2,3(1H,4H)-dione a) N-(Ethoxycarbonylmethyl)-N-(2,4-dinitro-1-naphthyl)-4-methylphenylsulfonamide 60 g (155 mmol) of N-(2,4-dinitro-1-naphthyl)-4-methylphenylsulfonamide (J. Soc. Chem. 1935, 1855) were dissolved in 500 ml of anhydrous dimethylformamide under protective gas and 19.1 g (170 mmol) of potassium tert-butanolate were added a little at a time. The mixture was stirred at room temperature for about 30 minutes, and then 25.9 g (155 mmol) of ethyl bromoacetate dissolved in 50 ml of anhydrous dimethylformamide were added dropwise. The mixture was then heated at 100° C. for 90 minutes and, after cooling, poured into ice-water, and the aqueous phase was extracted with ethyl acetate. The organic phase was dried and concentrated under reduced pressure. The residue was heated with a mixture of 50 ml of toluene and 100 ml of ethanol and the resulting crystals were filtered off with suction to yield 55.7 g (76%) of the product.

Melting point 106°–107° C.

$^1$H-NMR (D$_6$-DMSO): δ=1.2 (3H); 2.4 (3H); 4.2 (2H); 4.7 (1H); 4.9 (1H); 7.25 (2H); 7.4 (2H); 7.7 (1H); 7.9 (1H); 8.3 (1H), 8.6 (1H) and 8.8 (1H) ppm.

b) Ethyl N-(2,4-dinitro-1-naphthyl)aminoacetate 50 g (106 mmol) of the product 33a were stirred in 200 ml of 90% strength sulfuric acid at room temperature for 1 h. The mixture was then poured into water and the precipitate was filtered off with suction to yield 28.4 g (85%) of the product. Melting point >305° C.

$^1$H-NMR (D$_6$-DMSO): δ=4.0 (2H); 7.6 (1H); 7.9 (1H); 8.6 (1H); 9.0 (1H) and about 11 (broad) ppm.

c) Ethyl N-(2,4-dinitro-1-naphthyl)-N-(ethoxycarbonylmethyl)oxamate 22 g (68.9 mmol) of the product 33b were dissolved in 250 ml of pyridine and, at room temperature, 8.1 ml (72.4 mmol) of ethyl oxalyl chloride were added dropwise. The mixture was stirred for 1 h and then concentrated under reduced pressure. The residue was partitioned between ethyl acetate and water, and the organic phase was dried and concentrated under reduced pressure to yield 21.3 g (74%) of the product. Melting point 101°–102° C.

$^1$H-NMR (D$_6$-DMSO): δ=0.8 (3H); 1.2 (3H); 3.9 (2H); 4.1 (2H); 4.3 (1H); 4.7 (1H); 7.9–8.1 (2H); 8.4 (1H); 8.6 (1H) and 8.8 (1H) ppm.

d) 9-Amino-4-ethoxycarbonylmethylbenzo[f]quinoxaline-2,3(1H,4H)-dione 20 g (47.7 mmol) of the product 33c were dissolved in a mixture of 10 ml of acetic acid and 300 ml of tetrahydrofuran and, after addition of 1.5 g of palladium/carbon (10%), hydrogenated. The mixture was filtered, and the filtrate was concentrated under reduced pressure to yield 13.8 g (93%) of the product. Melting point 294°–295° C. (decomposition).

$^1$H-NMR (D$_6$-DMSO): δ=1.2 (3H); 4.2 (2H); 5.8 (2H); 6.0 (2H, NH, broad); 6.5 (1H); 7.3 (1H); 7.4 (1H); 7.8 (1H); 8.2 (1H) and 12.0 (1H) ppm.

e) 9-(2,3-Dimethyl-1-pyrrolyl)-4-ethoxycarbonylmethylbenzo[f]quinoxaline-2,3(1H,4H)-dione 13.0 g (41.5 mmol) of the product 33d and 4.9 ml (41.5 mmol) of 2,5-hexanedione were refluxed in 150 ml of acetic acid for 1 h. The mixture was then concentrated under reduced pressure, the residue was partitioned between ethyl acetate and water, and the organic phase was dried and concentrated under reduced pressure. The residue was purified by chromatography on silica gel (mobile phase: toluene/acetone 2:1) to yield 8.3 g (52%) of the product. Melting point 132°–133° C. (decomposition).

$^1$H-NMR (D$_6$-DMSO): δ=1.2 (3H); 1.8 (6H); 4.2 (2H); 5.1 (2H); 5.9 (2H); 6.9 (1H); 7.3 (1H); 7.5 (1H); 7.6 (1H); 8.1 (1H) and 12.3 (broad) ppm.

EXAMPLE 34

4-Carboxymethyl-9-(2,5-dimethyl-1-pyrrolyl)benzo[f]-quinoxaline-2,3(1H,4H)-dione 7.0 g (17.9 mmol) of Example 33 were dissolved in 100 ml of tetrahydrofuran, and a solution of 1.3 g (53.7 mmol) of lithium hydroxide in 30 ml of water was added. The mixture was stirred at room temperature for 4 h. The organic solvent was then removed under reduced pressure, and the resulting aqueous phase was diluted with dilute hydrochloric acid and extracted with ethyl acetate. This organic phase was dried and concentrated under reduced pressure to yield 4.8 g (74%) of the product. Melting point >210° C. (decomposition).

$^1$H-NMR (D$_6$-DMSO): δ=1.8 (6H); 4.9 (1H); 5.7 (1H); 5.9 (2H); 6.9 (1H); 7.4–7.7 (2H); 7.85+8.5 (1H); 8.1–8.2 (1H) and 12.3 (1H) ppm.

EXAMPLE 35

4-Benzylcarbamoylmethyl-9-(2,5-dimethyl-1-pyrrolyl)benzo-[f]quinoxaline-2,3(1H,4H)-dione 1.3 g (3.6 mmol) of Example 34 and 0.43 ml (3.9 mmol) of benzylamine were dissolved in 30 ml of anhydrous dimethylformamide. At 0° C., 0.85 ml (3.9 mmol) of diphenylphosphoryl azide dissolved in 10 ml of anhydrous dimethylformamide, and 1.1 ml (7.9 mmol) of triethylamine were successively added dropwise. The mixture was stirred at room temperature for 16 h and then poured into ice-water and extracted with ethyl acetate. The organic phase was dried and concentrated under reduced pressure. The residue was purified by chromatography on silica gel (mobile phase: methylene chloride/methanol=20:3) to yield 1.1 g (70%) of the product.

Melting point >290° C.

$^1$H-NMR (D$_6$-DMSO): δ=1.8 (6H); 4.4 (2H); 4.95 (2H); 5.9 (2H); 6.8 (1H); 7.2–7.5 (8H); 9.05 (1H) and about 12.5 (broad) ppm.

EXAMPLE 36

6-Chloro-1-cyclohexyl-7-(1-pyrrolyl)2,3(1H,4H)-quinoxalinedione a) 4–Chloro-N-cyclohexyl-2-nitroaniline 51.5 g (0.27 mol) of 2,5-dichloronitrobenzene, 22.3 g (0.27 mol) of cyclohexylamine, 74.6 g (0.54 mol) of potassium carbonate and 0.5 g of 18-crown-in 300 ml of dimethylformamide were heated at 100° C. for 4 h. The mixture was then poured into water and extracted with ethyl acetate. The organic phase was dried and concentrated under reduced pressure. The residue was recrystallized from i-propanol, resulting in 42.3 g (62%) of the product. Melting point 101°–103° C.

$^1$H-NMR (D$_6$-DMSO): δ=1.2–2.0 (10H); 3.7 (1H); 7.1 (1H); 7.5 (1H); 8.0 (1H) and 8.05 (1H) ppm.

b) 2-Amino-4-chloro-N-cyclohexylaniline 41.6 g (0.16 mol) of 4-chloro-N-cyclohexyl-2-nitroaniline were dissolved in 400 ml of ethanol and, after addition of 4.2 g of Raney nickel, hydrogenated under 1 bar at 25° C. The mixture was then filtered and the filtrate was concentrated under reduced pressure to yield 37.3 g (100%) of the product.

$^1$H-NMR (D$_6$-DMSO): δ=1.0–2.0 (10H); 3.1 (1H); 4.0–5.0 (3H, broad) and 6.3–6.6 (3H) ppm.

c) 6-Chloro-1-cyclohexyl-2,3(1H,4H)-quinoxalinedione 34.5 g (0.15 mol) of 2-amino-4-chloro-N-cyclohexylaniline were refluxed in 500 ml of diethyl oxalate for 4 h. After cooling, the precipitate was filtered off with suction, washed with n-pentane and dried to yield 26.8 g (63%) of the product. Melting point 265°–266° C.

$^1$H-NMR (D$_6$-DMSO): δ=1.1–1.9 (8H); 2.3–2.5 (2H); 4.4 (1H); 7.1 (2H); 7.6 (1H); and 12 (broad) ppm.

d) 6-Chloro-1-cyclohexyl-7-nitro-2,3(1H,4H)-quinoxalinedione 26.3 g (94 mmol) of 6-Chloro-1-cyclohexyl-2,3(1H,4H)-quinoxalinedione were dissolved in 275 ml of concentrated sulfuric acid and then, at 0° C., 9.5 g (94 mmol) of potassium nitrate were added a little at a time. The mixture was then stirred at 0° C. for 30 min and at 25° C. for 2 h and poured into ice-water. The precipitate was filtered off with suction to yield 29.5 g (97%) of the product.

Melting point >300° C.

$^1$H-NMR (D$_6$-DMSO): δ=1.1–1.9 (8H); 2.3–2.5 (2H); 4.4 (1H); 7.3 (1H) and about 12.5 (1H) ppm.

e) 7-Amino-6-chloro-1-cyclohexyl-2,3(1H,4H)-quinoxalinedione (e1) and 7-amino-1-cyclohexyl-2,3(1H,4H)-quinoxalinedione (e2)

28.9 g (89 mmol) of 6-Chloro-1-cyclohexyl-7-nitro-2,3 (1H,4H)-quinoxalinedione were dissolved in 300 ml of tetrahydrofuran/methanol/dimethylformamide (3:3:1) and, after addition of 3 g of palladium/carbon (10%), hydrogenated. The mixture was filtered, the carbon was washed with methanolic ammonia solution, and the combined filtrates were concentrated under reduced pressure. The residue was chromatographed on silica gel with the mobile phase toluene/acetone/glacial acetic acid (10:10:1) to yield 2.2 g (8%) of product e1 and 18.5 g (80%) of product e2.

e1

$^1$H-NMR (D$_6$-DMSO): δ=1.1–2.0 (8H); 2.3–2.5 (2H); 4.4 (1H); about 5.2 (2H, broad); 7.0 (1H); 7.1 (1H) and about 11.5 (broad) ppm.

e2

$^1$H-NMR (D$_6$-DMSO): δ=1.1–2.0 (8H); 2.3–2.5 (2H); 4.4 (1H); about 5.1 (2H, broad); 6.4 (1H); 6.8 (1H); 6.9 (1H) and about 11.5 (broad) ppm.

f) 6-Chloro-1-cyclohexyl-7-(1-pyrrolyl)-2,3(1H,4H)-quinoxalinedione 1.9 g (6.3 mmol) of 7-amino-6-chloro-1-cyclohexyl-2,3 (1H,4H)-quinoxalinedione (36 e1) and 1.1 g (7.9 mmol) of 2,5-dimethoxytetrahydrofuran in 40 ml of glacial acetic acid were refluxed for 2 h. The mixture was then poured into ice-water, and the precipitate was filtered off with suction to yield 2.0 g (90%) of Example 36. Melting point 216°–218° C. (decomposition).

$^1$H-NMR (D$_6$-DMSO): δ=1.1–2.0 (8H); 2.3–2.5 (2H); 4.4 (1H); 6.3 (2H); 7.0 (2H); 7.3 (1H); 7.6 (1H) and 12.0 (1H) ppm.

EXAMPLE 37

1-Cyclohexyl-6-nitro-7-(1-pyrrolyl)-2,3(1H,4H)-quinoxalinedione a) 7-Acetamido-1-cyclohexyl-2,3(1H,4H)-quinoxalinedione 18.3 g (70 mmol) of 7-amino-1-cyclohexyl-2,3 (1H,4H)-quinoxalinedione (product e2 from Example 36) were dissolved in 250 ml of acetic acid and, after a spatula tip of 4-(N,N-dimethylamino)pyridine had been added, 7.2 g (70 mmol) of acetic anhydride were added dropwise. The mixture was stirred at room temperature for 30 min and then the precipitate was filtered off with suction and dried to yield 20.8 g (98%) of the product. Melting point 227°–230° C. (decomposition).

$^1$H-NMR (D$_6$-DMSO): δ=1.1–1.9 (8H); 2.3–2.5 (2H); 4.5 (1H); 7.1 (1H); 7.3 (1H); 8.0 (1H); 10.0 (1H) and about 12.0 (broad) ppm.

b) 7-Amino-1-cyclohexyl-6-nitro-2,3(1H,4H)-quinoxalinedione 20.6 g (68 mmol) of 7-acetamido-1-cyclohexyl-2,3(1H, 4H)-quinoxalinedione were dissolved in 250 ml of concentrated sulfuric acid. Then, at 0°–5° C., 7.2 g (71 mmol) of potassium nitrate were added a little at a time. The mixture was then stirred at 0° C. for 30 min and at room temperature for 2 h and subsequently poured into 1.5 l of ice-water and then heated on a water bath for 4 h. The resulting precipitate was filtered off with suction. The filtrate was adjusted to pH 6 with a little ammonia solution and was extracted with methylene chloride. The organic phase was dried and concentrated under reduced pressure. This residue and the first precipitate were combined to yield 13.4 g (64%) of the product. Melting point >260° C.

$^1$H-NMR (D$_6$-DMSO): δ=1.1–2.0 (8H); 2.3–2.5 (2H); 4.3 (1H); 7.1 (1H); 7.1–7.4 (broad, 2H); 7.7 (1H) and about 11.5 (1H) ppm.

c) 1-Cyclohexyl-6-nitro-7-(1-pyrrolyl)-2,3(1H,4H)-quinoxalinedione 2.5 g (8.2 mmol) of 7-amino-1-cyclohexyl-6-nitro-2,3 (1H,4H)-quinoxalinedione and 1.4 g (10.3 mmol) of 2,5-dimethoxytetrahydrofuran in 50 ml of acetic acid were refluxed for 2 h. The mixture was then poured into ice-water, and the precipitate was filtered off with suction and crystallized from a little hot ethanol to yield 2.0 g (70%) of Example 37.

$^1$H-NMR (D$_6$-DMSO): δ=1.1–1.9 (8H); 2.3–2.5 (2H); 4.5 (1H); 6.25 (2H); 7.0 (2H); 7.6 (1H); 7.8 (1H) and about 12 (broad) ppm.

EXAMPLE 38

1-Cyclohexyl-7-(2-methoxycarbonyl-1-pyrrolyl)-6-nitro-2,3(1H,4H)-quinoxalinedione 4.5 g (14.8 mmol) of 7-amino-1-cyclohexyl-6-nitro-2,3 (1H,4H)-quinoxalinedione (product 37b) and 3.5 g (14.8 mmol) of 2-methoxycarbonyl-2,5-dimethoxytetrahydrofuran in 75 ml of acetic acid were refluxed for 2 h. The mixture was poured into ice-water, and the precipitate was filtered off with suction to yield 4.8 g (78%) of the product. Melting point 293° C. (decomposition).

$^1$H-NMR (D$_6$-DMSO): δ=1.1–1.9 (8H); 2.3–2.5 (2H); 3.6 (3H); 4.5 (1H); 6.4 (1H); 7.1 (1H); 7.2 (1H); 7.8 (1H); 7.9 (1H) and about 12 (broad) ppm.

EXAMPLE 39

9-Cyclohexyl-7,8(6H,9H)-dioxopyrazino[5,6-g] pyrrolo[1,2-c]quinoxalin-2(4H)one

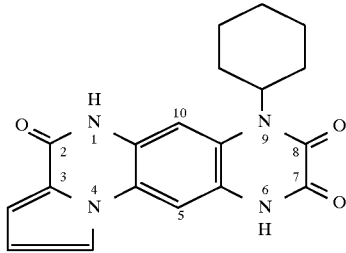

3.15 g (7.6 mmol) of 1-cyclohexyl-7-(2-methoxycarbonyl-1-pyrrolyl)-6-nitro-2,3(1H,4H)-quinoxalinedione were dissolved in 200 ml of acetic acid and, at 80° C., 4.3 g (7.6 mmol) of iron powder were added a little at a time. The mixture was refluxed for a further 2 h and then concentrated under reduced pressure, and the residue was dispersed in 2M hydrochloric acid. The precipitate was filtered off with suction to yield 2.4 g (91%) of the product. Melting point >300° C.

$^1$H-NMR (D$_6$-DMSO): δ=1.1–2.0 (8H); 2.3–2.5 (2H); 4.6 (1H); 6.7 (1H); 7.0 (1H); 7.1 (1H); 7.9 (1H); 8.4 (1H); 11.3 (1H) and 12 (1H) ppm.

EXAMPLE 40

1-(2-Ethylbutyl)-6-nitro-7-(1-pyrrolyl)-2,3(1H,4H)-quinoxalinedione a) 4-Chloro-N-(2-ethylbutyl)-2-nitroaniline 50.0 g (0.26 mol) of 2,5-dichloro-1-nitrobenzene, 71.9 g (0.52 mol) of potassium carbonate, 45.6 g (0.455 mol) of 2-ethylbutylamine and 0.5 g of 18-crown-6 in 250 ml of dimethylformamide were heated at 80° C. for 4 h. The mixture was then poured into a large quantity of ice-water, and the precipitate was filtered off with suction, dried and recrystallized from methanol to yield 41.8 g (63%) of product.

$^1$H-NMR (D$_6$-DMSO): δ=0.9 (6H); 1.3 (4H); 1.6 (1H); 3.3 (2H); 7.1 (1H); 7.5 (1H); 8.0 (1H) and 8.1 (1H) ppm.

b) 2-Amino-4-chloro-N-(2-ethylbutyl)aniline 40 g (0.156 mol) of 4-chloro-N-(2-ethylbutyl)-2-nitroaniline were dissolved in 500 ml of ethanol and, after addition of 4 g of Raney nickel, hydrogenated under 1 atm at room temperature. The mixture was then filtered and the filtrate was concentrated under reduced pressure to yield 35 g (98%) of the product.

$^1$H-NMR (D$_6$-DMSO): δ=0.8 (6H); 1.4 (4H); 1.5 (1H); 2.8 (2H); 4.2 (1H); 4.8 (broad, 2H), 6.3 (1H); 6.4 (1H) and 6.5 (1H) ppm.

c) 6-Chloro-1-(2-ethylbutyl)-2,3(1H,4H)-quinoxalinedione 35 g (0.124 mol) of 2-amino-4-chloro-N-(2-ethylbutyl) aniline were refluxed in 350 ml of diethyl oxalate for 2.5 h. After cooling, the precipitate was filtered off with suction and dried to yield 33 g (76%) of the product. Melting point 253°–255°C.

$^1$H-NMR (D$_6$-DMSO): δ=0.9 (6H); 1.3 (4H); 1.7 (1H); 4.0 (2H); 7.2 (1H); 7.25 (1H) and 7.3 (1H) ppm.

d) 6-Chloro-1-(2-ethylbutyl)-7-nitro-2,3(1H,4H)-quinoxalinedione 30 g (0.106 mol) of 6-chloro-1-(2-ethylbutyl)-2,3(1H,4H)-quinoxalinedione were dissolved in 350 ml of concentrated sulfuric acid and cooled to 0°C. Then, at 0° C., 10.8 g of potassium nitrate were added a little at a time, and the solution was stirred for 1.5 h. The mixture was then poured into ice-water, and the precipitate was filtered off with suction, washed with water and dried to yield 31 g (91%) of the product. Melting point 232°–233° C.

$^1$H-NMR (D$_6$-DMSO): δ=0.9 (6H); 1.3 (4H); 1.8 (1H); 4.1 (2H); 7.3 (1H); 8.0 (1H) and 12.5 (1H) ppm.

e) 7-Amino-1-(2-ethylbutyl)-2,3 (1H,4H)-quinoxalinedione 36.0 g (0.112 mol) of 6-chloro-1-(2-ethylbutyl)-7-nitro-2,3(1H,4H)-quinoxalinedione were dissolved in 500 ml of isopropanol under nitrogen, and a solution of 70.6 g (1.12 mol) of ammonium formate in 100 ml of water was added. 3.5 g of palladium/carbon (10%) were added and the mixture was refluxed for 1 h. It was subsequently filtered, and the filtrate was concentrated under reduced pressure. The residue was partitioned between aqueous sodium bicarbonate solution and ether. The ether phase was separated off, dried and concentrated under reduced pressure.

Melting point 246° C. (decomposition).

$^1$H-NMR (D$_6$-DMSO): δ=0.9 (6H); 1.3 (4H); 1.9 (1H); 4.0 (2H); 5.2 (2H); 6.4 (1H); 6.5 (1H) and 6.9 (1H) ppm.

f) 7-Acetamido-1-(2-ethylbutyl)-2,3(1H,4H)-quinoxalinedione 29.0 g (0.111 mol) of 7-amino-1-(2-ethylbutyl)-2,3(1H,4H)-quinoxalinedione were dissolved in 200 ml of acetic acid. A spatula tip of 4-(N,N-dimethylamino)pyridine was added and then 11.4 g (0.111 mol) of acetic anhydride were added dropwise. The mixture was stirred at room temperature for 30 minutes and then poured into ice-water, and the precipitate was filtered off with suction and dried to yield 22.5 g (67%) of the product.

Melting point 168°–170° C.

$^1$H-NMR (D$_6$-DMSO): δ=0.9 (6H); 1.3 (4H); 1.9 (1H); 2.1 (3H); 4.0 (2H); 7.1 (1H); 7.2 (2H); 7.9 (1H); 10.1 (1H) and about 11.5 (broad) ppm.

g) 7-Acetamido-1-(2-ethylbutyl)-6-nitro-2,3(1H,4H)-quinoxalinedione 21.0 g (69.2 mmol) of 7-acetamido-1-(2-ethylbutyl)-2,3(1H,4H)-quinoxalinedione were dissolved in 250 ml of concentrated sulfuric acid and, at 0°–5° C., 7.0 g (69.2 mmol) of potassium nitrate were added a little at a time. The mixture was stirred for 1 h and a further 3.5 g (34.6 mmol) of potassium nitrate were added, and the mixture was stirred at room temperature for 16 h. It was then poured into ice-water, and the precipitate was filtered off with suction and dried to yield 18.0 g (75%) of the product, which was immediately processed further.

h) 7-Amino-1-(2-ethylbutyl)-6-nitro-2,3(1H,4H)-quinoxalinedione 18.0 g (51.6 mmol) of 7-acetamido-1-(2-ethylbutyl)-2,3(1H,4)-quinoxalinedione were refluxed in a mixture of 50 ml of ethanol and 300 ml of 2M hydrochloric acid for 1.5 h. The solution was then concentrated under reduced pressure, and the residue was partitioned between water and ethyl acetate. The organic phase was dried and concentrated under reduced pressure to yield 13.0 g (82%) of the product.

$^1$H-NMR (D$_6$-DMSO): δ=0.9 (6H); 1.3 (4H); 1.8 (1H); 3.9 (3H); 6.8 (1H); 7.2–7.6 (broad, 2H); 7.8 (1H) and 11.9 (1H) ppm.

i) 1-(2-Ethylbutyl)-6-nitro-7-(1-pyrrolyl)-2,3(1H,4H)-quinoxalinedione 2.5 g (8.2 mmol) of 7-amino-1-(2-ethylbutyl)-6-nitro-2,3(1H,4H)-quinoxalinedione and 1.1 g (8.2 mmol) of 2,5-dimethoxytetrahydrofuran were refluxed in 100 ml of acetic acid for 1 h. The mixture was then poured into ice-water, and the precipitate was filtered off with suction, washed with water and dried to yield 0.8 g (31%) of the product. Melting point 154°–155° C.

$^1$H-NMR (D$_6$-DMSO): δ=0.8 (6H); 1.3 (4H); 1.8 (1H); 4.1 (2H); 6.3 (2H); 6.9 (2H); 7.3 (1H); 7.8 (1H) and 12.3 (1H) ppm.

EXAMPLE 41

1-(2-Ethylbutyl)-7-(2-methoxycarbonyl-1-pyrrolyl)-6-nitro-2,3(1H,4H)-quinoxalinedione 3.0 g (9.8 mmol) of 7-amino-1-(2-ethylbutyl)-6-nitro-2,3(1H,4H)-quinoxalinedione (Example 40 h) and 1.8 g (9.8 mmol) of 2-methoxycarbonyl-2,5-dimethoxytetrahydrofuran were refluxed in 150 ml of concentrated acetic acid for 1 h. The mixture was then poured into ice-water, and the precipitate was filtered off with suction to yield 1.1 g (28%) of the product. Melting point 240°–241° C.

$^1$H-NMR (D$_6$-DMSO): δ=0.8 (6H); 1.3 (4H); 1.8 (1H); 3.6 (3H); 4.2 (2H); 6.4 (1H); 7.1 (1H); 7.3 (1H); 7.4 (1H); 8.0 (1H) and about 12.5 (1H) ppm.

EXAMPLE 42

1-Cyclopropyl-6-nitro-7-(1-pyrrolyl)-2,3(1H,4H)-quinoxalinedione 2,5-Dibromo-1-nitrobenzene and cyclopropylamine were reacted as in Example 40 (a–i).

$^1$H-NMR (D$_6$-DMSO): δ=0.8 (2H); 1.3 (2H); 3.0 (1H); 6.3 (2H); 6.9 (2H); 7.6 (1H); 7.8 (1H) and 12.5 (1H) ppm.

EXAMPLE 43

7-Bromo-9-(2,5-dimethyl-1-pyrrolyl)benzo[f] quinoxaline-2,3(1H,4H)-dione a) 6-Bromo-2-methoxy-1-nitronaphthalene 10 ml of 98% strength nitric acid dissolved in 70 ml of acetic acid were added dropwise to 50 g (0.21 mol) of 6-bromo-2-methoxynaphthalene dissolved in 350 ml of acetic acid at room temperature. The mixture was heated to 50° C. and, after the product had crystallized, cooled. The precipitate was filtered off with suction to yield 53.1 g (90%) of the product. Melting point 156°–157° C.

$^1$H-NMR (D$_6$-DMSO): δ=4.1 (3H); 7.5 (1H); 7.7–7.8 (2H); 8.2 (1H) and 8.3 (1H) ppm.

b) 6-Bromo-1-nitro-2-naphthylamine 10 g (35.4 mmol) of the product 43a in 100 ml of dimethylformamide were heated in the presence of 0.8 mol of ammonia in an autoclave at 100° C. for 24 h. The mixture was then concentrated under reduced pressure, and the precipitate was dispersed in water and filtered off with suction to yield 9.3 g (98%) of the product. Melting point >175° C. (decomposition).

$^1$H-NMR (D$_6$-DMSO): δ=7.2 (1H); 7.7 (1H); 7.8 (1H); 8.0 (1H); 8.05 (2H) and 8.5 (1H) ppm.

c) 2-Amino-6-bromo-1-naphthylamine 9 g (33.7 mmol) of the product 43b were dissolved in 250 ml of ethanol and, after addition of 2 g of Raney nickel, hydrogenated. The mixture was then filtered, and the filtrate was concentrated under reduced pressure to yield 7.4 g (92%) of the product. Melting point 159°–160° C. (decomposition).

$^1$H-NMR (D$_6$-DMSO): δ=about 5 (4H, broad); 7.0 (2H); 7.3 (1H) and 7.8–7.9 (2H) ppm.

d) 7-Bromobenzo[f]quinoxaline-2,3(1H,4H)-dione 7 g (29.5 mmol) of the product 43c were refluxed in 300 ml of diethyl oxalate for 3 h. After cooling, the precipitate was filtered off with suction, washed with ethanol and dried to yield 5.9 g (69%) of the product.

$^1$H-NMR (D$_6$-DMSO): δ=7.4 (1H); 7.7 (2H); 8.2 (1H); 8.5 (1H) and 12.3 (2H) ppm.

e) 7-Bromo-9-nitrobenzo[f]quinoxaline-2,3(1H,4H)-dione 5.5 g (18.9 mmol) of the product 43d were suspended in 150 ml of acetic acid. 25 ml of 65% strength nitric acid were added dropwise at room temperature, and then the mixture was heated at 100° C. for 30 minutes. After cooling, the precipitate was filtered off with suction to yield 4.7 g (74%) of the product.

$^1$H-NMR (D$_6$-DMSO): δ=7.65 (1H); 8.4 (1H); 8.75 (1H); 9.0 (1H) and 11.8 (broad) ppm.

f) 9-Amino-7-bromobenzo[f]quinoxaline-2,3(1H,4H)-dione 4.4 g (13.1 mmol) of the product 43e were dissolved in a mixture of 100 ml of methanol and 200 ml of tetrahydrofuran and, after addition of 1 g of Raney nickel, hydrogenated. The mixture was then filtered, and the filtrate was concentrated under reduced pressure to yield 3.7 g (93%) of the product.

Melting point >260° C.

$^1$H-NMR (D$_6$-DMSO): δ=about 5.9 (2H, broad); 6.6 (1H); 7.6 (1H); 8.0 (1H); 8.3 (1H) and about 12 (broad) ppm.

g) 7-Bromo-9-(2,5-dimethyl-1-pyrrolyl)benzo[f]quinoxaline-2,3(1H,4H)-dione 3.1 g (10.1 mmol) of the product 43f and 1.2 ml (10.1 mmol) of 2,5-hexanedione were refluxed in 150 ml of acetic acid for 30 minutes. The mixture was then concentrated under reduced pressure, and the residue was dispersed in water and filtered off with suction to yield 2.8 g (75%) of the product.

Melting point >270° C.

$^1$H-NMR (D$_6$-DMSO): δ=1.8 (6H); 5.9 (2H); 6.9 (2H); 7.3 (1H); 7.8 (1H); 8.6 (1H) and 12.2 (broad) ppm.

EXAMPLE 44

7-Chloro-6-(2,5-dimethyl-1-pyrrolyl)-1-(methoxycarbonylmethyl)-2,3(1H,4H)-quinoxalinedione a) N-(5-Chloro-2-nitrophenyl)glycine 25 g (0.13 mol) of 2,4-dichloro-1-nitrobenzene, 19.5 g (0.26 mol) of glycine and 18 g (0.13 mol) of potassium carbonate were heated in 200 ml of dimethylformamide at 120° C. for 3 h. The mixture was then poured into ice-water, acidified with 1M hydrochloric acid and extracted with ethyl acetate. The organic phase was dried and concentrated under reduced pressure. The residue was purified by chromatography on silica gel (mobile phase: toluene/acetone/acetic acid=20:10:1) to yield 19.7 g (66%) of the product. Melting point 147°–148° C.

$^1$H-NMR (D$_6$-DMSO): δ=4.2 (2H); 6.7 (1H); 7.0 (1H); 8.1 (1H); 8.4 (1H) and about 12.5 (broad) ppm.

b) N-(2-Amino-5-chlorophenyl)glycine 19.5 g (84.6 mmol) of N-(5-chloro-2-nitrophenyl)glycine were dissolved in 250 ml of ethanol and, after addition of 5 g of Raney nickel, hydrogenated under 1 bar at 45°–50° C. The mixture was then filtered, and the filtrate was evaporated under reduced pressure to yield 15.6 g (93%) of the product.

$^1$H-NMR (D$_6$-DMSO): δ=3.7 (2H); 6.2 (1H); 6.5–6.8 (3H) and 10.2 (1H) ppm.

c) 1-(Carboxymethyl)-7-chloro-2,3(1H,4H)-quinoxalinedione 15 g (75 mmol) of N-(2-amino-5-chlorophenyl)glycine and 21 ml (150 mmol) of triethylamine were dissolved in 250 ml of anhydrous tetrahydrofuran and, at 0° C., a solution of 18.2 ml (16.4 mmol) of ethyl oxalyl chloride and 30 ml of anhydrous tetrahydrofuran was added dropwise. The mixture was stirred at 0° C. for one hour and at room temperature for a further two and was then concentrated under reduced pressure. The residue was partitioned between water and methylene chloride, the organic phase was dried and concentrated under reduced pressure, and the residue was crystallized from a little ethanol. This product was refluxed in a mixture of 200 ml of ethanol and 250 ml of concentrated hydrochloric acid for 1 h. The mixture was then poured into ice and the precipitate was filtered off with suction to yield 13.7 g (93%) of the product. Melting point >285° C.

$^1$H-NMR (D$_6$-DMSO): δ=4.9 (2H); 7.0–7.3 (2H); 7.4 (1H); 12.3 (1H) and about 13 (broad) ppm.

d) 1-Carboxymethyl-7-chloro-6-nitro-2,3(1H,4H)-quinoxalinedione 13.0 g (51 mmol) of 1-(carboxymethyl)-7-chloro-2,3(1H, 4H)-quinoxalinedione were dissolved in 150 ml of concentrated sulfuric acid and, at 0° C., 4.3 g (51 mmol) of sodium nitrate were added a little at a time. The mixture was stirred at room temperature for 2 h and then poured into ice-water, and the precipitate was filtered off with suction to yield 10.2 g (67%) of the product. Melting point >280° C.

$^1$H-NMR (D$_6$-DMSO): δ=5.0 (2H); 7.8 (1H); 7.9 (1H) and 12.5 (1H) ppm.

e) 7-Chloro-1-(methoxycarbonylmethyl)-6-nitro-2,3(1H, 4H)-quinoxalinedione 10 g (33.4 mmol) of 1-carboxymethyl-7-chloro-2,3(1H, 4H)-quinoxalinedione were refluxed in a mixture of 2 ml of concentrated sulfuric acid and 200 ml of ethanol for 1 h. After cooling, the precipitate was filtered off with suction to yield 11.5 g of the product. Melting point >260° C.

$^1$H-NMR (D$_6$-DMSO): δ=1.25 (3H); 4.2 (2H); 5.0 (2H); 7.8 (1H); 7.9 (1H) and 12.5 (1H) ppm.

f) 6-Amino-7-chloro-1-(methoxycarbonylmethyl)-2,3(1H, 4H)-quinoxalinedione 10 g (30.5 mmol) of 7-chloro-1-(methoxycarbonylmethyl)-6-nitro-2,3(1H,4H)-quinoxalinedione were dissolved in 300 ml of dimethylformamide and, after addition of 5 g of Raney nickel, hydrogenated under 1 bar at room temperature. The mixture was then filtered and the filtrate was concentrated under reduced pressure to yield 8.6 g (95%) of the product. Melting point >260° C.

$^1$H-NMR (D$_6$-DMSO): δ=1.2 (3H); 4.2 (2H); 4.85 (2H); 5.45 (2H); 6.6 (1H); 7.25 (1H) and 12 (1H) ppm.

g) 7-Chloro-6-(2,5-dimethyl-1-pyrrolyl)-1-(methoxycarbonylmethyl)-2,3(1H,4H)-quinoxalinedione 6.0 g (20.2 mmol) of 6-amino-7-chloro-1-(methoxycarbonylmethyl)-2,3(1H,4H)-quinoxalinedione and 2.4 ml (20.2 mmol) of 2,5-hexanedione were refluxed in 75 ml of glacial acetic acid for 0.5 h. The mixture was then poured into ice-water and the precipitate was filtered off with suction to yield 5.5 g (74%) of the product.

$^1$H-NMR (D$_6$-DMSO): δ=1.2 (3H); 1.9 (6H); 4.2 (2H); 5.0 (2H); 5.8 (2H); 7.1 (1H); 7.8 (1H) and 12.3 (broad) ppm.

EXAMPLE 45

1-(Carboxymethyl)-7-chloro-6-(2,5-dimethyl-1-pyrrolyl)-2,3(1H,4H)-quinoxalinedione 4.0 g (10.6 mmol) of 7-chloro-6-(2,5-dimethyl-1-pyrrolyl)-1-(methoxycarbonylmethyl)-2,3(1H,4H)-quinoxalinedione (Example 44) were dissolved in 100 ml of tetrahydrofuran, and a solution of 0.76 g (31.9 mmol) of lithium hydroxide in 15 ml of water was added. The mixture was stirred at room temperature for 2 h and then the organic solvent was removed under reduced pressure, and the aqueous phase was acidified with 1M hydrochloric acid. The precipitate was filtered off with suction to yield 3.1 g (84%) of the product. Melting point >265° C.

$^1$H-NMR (D$_6$-DMSO): δ=1.9 (6H); 4.9 (2H); 5.8 (2H); 7.1 (1H); 7.7 (1H) and 12.5 (1H) ppm.

EXAMPLE 46

1-Benzylcarbamoylmethyl-7-chloro-6-(2,5-dimethyl-1-pyrrolyl)-2,3(1H,4H)-quinoxalinedione 1.3 g (3.7 mmol) of 1-(carboxymethyl)-7-chloro-6-(2,5-dimethyl-1-pyrrolyl)-2,3(1H,4H)-quinoxalinedione and 1.6 ml (12.3 mmol) of benzylamine were dissolved in 30 ml of dimethylformamide and, at 0° C., a solution of 0.89 ml (4.1 mmol) of diphenylphosphoryl azide in 10 ml of dimethylformamide was added dropwise. The mixture was stirred at room temperature for 16 h and then poured into ice-water, and the aqueous phase was extracted with ethyl acetate. The organic phase was dried and concentrated under reduced pressure. The residue was purified by chromatography on silica gel (mobile phase: toluene/acetone=1:1) to yield 1.1 g (67%) of the product.

Melting point 244° C.

$^1$H-NMR (D$_6$-DMSO): δ=1.8 (6H); 4.3 (2H); 4.9 (2H); 5.8 (2H); 7.1 (1H); 7.2–7.4 (5H); 7.5 (1H); 8.7 (1H) and 12.5 (1H) ppm.

EXAMPLE 47

1-(Carboxymethyl)-9-(2,5-dimethyl-1-pyrrolyl)benzo[f]-quinoxaline-2,3(1H,4H)-dione 13.0 g (33.2 mmol) of Example 31 were dissolved in 200 ml of tetrahydrofuran, and a solution of 2.4 g (99.6 mmol) of lithium hydroxide in 100 ml of water was added. The mixture was stirred at room temperature for 2 h and then the tetrahydrofuran was removed under reduced pressure, and the aqueous phase was acidified by adding 11 ml of concentrated hydrochloric acid. The precipitate was filtered off with suction to yield 10.7 g (89%) of the product. Melting point 236°–237° C. (decomposition).

$^1$H-NMR (D$_6$-DMSO): δ=1.8 (6H); 5.1 (2H); 5.9 (2H); 6.9 (1H); 7.6 (1H); 7.8 (2H); 8.7 (1H); 12.5 (1H) and about 13.5 (broad) ppm.

EXAMPLE 48

1-Benzylcarbamoylmethyl-9-(2,5-dimethyl-1-pyrrolyl)benzo-[f]quinoxaline-2,3(1H,4H)-dione 1.5 g (4.1 mmol) of Example 47 and 0.5 ml (4.5 mmol) of benzylamine were dissolved in 30 ml of anhydrous dimethylformamide. At 0° C., 1 ml (4.5 mmol) of diphenylphosphoryl azide dissolved in 10 ml of dimethylformamide, and 1.25 ml (9.1 mmol) of triethylamine were successively added dropwise. The mixture was then stirred at room temperature for 3 h. The solution was subsequently partitioned between 2M hydrochloric acid and ethyl acetate. The organic phase was dried and concentrated under reduced pressure. The residue was crystallized from ethanol/tetrahydrofuran. Yield: 1.25 g (67%); melting point 243°–244° C.

$^1$H-NMR (D$_6$-DMSO): δ=1.8 (6H); 4.3 (2H); 5.1 (2H); 5.9 (2H); 6.9 (1H); 7.1–7.4 (5H); 7.5–7.8 (3H); 8.7 (2H) and 12.5 (1H) ppm.

EXAMPLE 49

1-Phenylcarbamoylmethyl-9-(2,5-dimethyl-1-pyrrolyl)benzo-[f]quinoxaline-2,3(1H,4H)-dione 1.15 g (3.2 mmol) of Example 47 and 0.32 ml (3.5 mmol) of aniline were reacted as in Example 48. The resulting product was purified by chromatography on silica gel (mobile phase: toluene/acetone/acetic acid=20:10:1). Yield: 0.37 g (27%). Melting point >260° C.

$^1$H-NMR (D$_6$-DMSO) δ=1.8 (6H); 5.5 (2H); 6.0 (2H); 7.1 (2H); 7.3 (2H); 7.5 (2H); 7.8 (1H); 8.0 (1H); 8.2 (1H); 9.9 (1H) and 10.4 (1H) ppm.

EXAMPLE 50

1-(Benzyloxycarbonylmethyl)-9-(2,5-dimethyl-1-pyrrolyl)-benzo[f]quinoxaline-2,3(1H,4H)-dione 1.3 g (3.6 mmol) of Example 47 and 0.41 ml (3.9 mmol) of benzyl alcohol were reacted as in Example 48. The resulting product was purified by chromatography on silica gel (mobile phase: toluene/acetone/acetic acid=10:10:1). Yield: 1.0 g (63%).

$^1$H-NMR (D$_6$-DMSO): δ=1.8 (6H); 5.2 (2H); 5.3 (2H); 5.9 (2H); 6.9 (1H); 7.3 (5H); 7.5 (1H); 7.7 (1H); 7.75 (1H); 8.8 (1H) and about 12.5 (broad) ppm.

EXAMPLE 51

1-Ethylcarbamoylmethyl-9-(2,5-dimethyl-1-pyrrolyl)benzo-[f]quinoxaline-2,3(1H,4H)-dione 0.8 g (2.0 mmol) of Example 31 were refluxed in 200 ml of a 10% strength ethanolic ethylamine solution for 40 h. The mixture was then concentrated under reduced pressure, and the residue was purified by chromatography on silica gel (mobile phase: toluene/acetone/acetic acid=20:10:1). Yield: 0.41 g (52%). Melting point >285° C.

$^1$H-NMR (D$_6$-DMSO): δ=0.95 (3H); 1.8 (6H); 3.1 (2H); 4.9 (2H); 5.9 (2H); 6.9 (1H); 7.4 (1H); 7.55 (1H); 7.7 (1H); 8.2 (1H); 8.8 (1H) and 12.4 (broad) ppm.

EXAMPLE 52

1-(Ethoxycarbonylmethyl)-6-nitro-7-(1-pyrrolyl)-2,3(1H,4H)-quinoxalinedione a) N-(4-Chloro-2-nitrophenyl)glycine 26.2 g (0.137 mol) of 2,5-dichloro-1-nitrobenzene, 20.6 g (0.274 mol) of glycine and 18.9 g (0.137 mol) of potassium carbonate in 200 ml of diethylene glycol were heated at 120° C. for 1 h. After cooling, 100 ml of water were added and the solution was acidified with 1M hydrochloric acid. The precipitate was filtered off with suction to yield 17.1 g (54%) of the product.

$^1$H-NMR (D$_6$-DMSO): δ=4.2 (2H); 6.9 (1H); 7.5 (1H); 8.1 (1H); 8.4 (1H) and about 13 (broad) ppm.

b) Ethyl N-(4-chloro-2-nitrophenyl)aminoacetate 87.1 g (0.38 mol) of N-(4-chloro-2-nitrophenyl)glycine were suspended in 500 ml of 10% strength ethanolic sulfuric acid and heated to 80° C. The resulting clear solution was poured into 1.5 l of ice-water, and then the solution was neutralized with concentrated ammonia solution and sodium bicarbonate solution. The precipitate was filtered off with suction to yield 84.4 g (89%) of the product.

$^1$H-NMR (D$_6$-DMSO): δ=1.2 (3H); 4.2 (2H); 4.3 (2H); 7.0 (1H); 7.5 (1H); 8.0 (1H) and 8.4 (1H) ppm.

c) Ethyl N-(4-chloro-2-nitrophenyl)-N-(ethoxycarbonylmethyl)oxamate 86.1 g (0.33 mol) of the compound of Example 52b were dissolved in 350 ml of pyridine and, at room temperature, 67.6 g (0.495 mol) of ethyl oxalyl chloride were added dropwise. The mixture was stirred at room temperature for 16 h and then poured into ice-water and acidified with 4M hydrochloric acid. The precipitate was filtered off to yield 120 g of impure product.

$^1$H-NMR (D$_6$-DMSO): δ=1.1–1.3 (6H); 4.0 (2H); 4.2 (2H); 4.5 (1H); 4.6 (1H); 7.7 (1H); 8.0 (1H) and 8.3 (1H) ppm.

d) 6-Chloro-1-(ethoxycarbonylmethyl)-2,3(1H,4H)-quinoxalinedione 101.3 g (0.28 mol) of ethyl N-(4-chloro-2-nitrophenyl)-N-(ethoxycarbonylmethyl)oxamate were dissolved in 1 l of acetic acid and heated to 80° C. Then 15.8 g (0.28 mol) of iron powder were added a little at a time. After 2 h, a further 15.8 g (0.28 mol) of iron powder were added. Half an hour later, the mixture was poured into ice-water and acidified with 4M hydrochloric acid. The precipitate was filtered off with suction to yield 75.7 g (95%) of the product.

$^1$H-NMR (D$_6$-DMSO): δ=1.2 (3H); 4.2 (2H); 5.0 (2H); 7.2 (2H); 7.3 (1H) and 12.3 (1H) ppm.

e) 6-Chloro-1-(ethoxycarbonylmethyl)-7-nitro-2,3(1H,4H)-quinoxalinedione 69.8 g (0.25 mol) of 6-chloro-1-(ethoxy-carbonylmethyl)-2,3(1H,4H)-quinoxalinedione were dissolved in 625 ml of concentrated sulfuric acid and, at 0° C., 25 g (0.25 mol) of potassium nitrate were added a little at a time. The cooling was then removed, and the mixture was stirred until reaction was complete. The mixture was poured into ice-water, and the precipitate was filtered off with suction to yield 77.8 g (95%) of the product.

$^1$H-NMR (D$_6$-DMSO): δ=1.3 (3H); 4.2 (2H); 5.0 (2H); 7.3 (1H); 8.2 (1H) and 12.5 (1H) ppm.

f) 7-Amino-1-(ethoxycarbonylmethyl)-2,3(1H,4H)-quinoxalinedione 84.3 g (0.26 mol) of 6-chloro-1-(ethoxy-carbonylmethyl)-7-nitro-2,3(1H,4H)-quinoxalinedione were suspended in 1.5 l of isopropanol, and 194.2 g (3.1 mol) of ammonium formate dissolved in 500 ml of water, and 8.5 g of palladium/carbon (10%) were successively added. The mixture was heated at 75° C. for 4 h and, after cooling, filtered, and the filter cake was extracted three times with 800 ml of dimethylformamide. The combined dimethylformamide phases were concentrated under reduced pressure, and the residue was washed with water to yield 53.2 g (79%) of the product.

$^1$H-NMR (D$_6$-DMSO): δ=1.2 (3H); 4.2 (2H); 4.8 (2H); 5.2 (broad, 2H); 6.4 (1H); 6.5 (1H); 6.9 (1H) and 12 (1H) ppm.

g) 7-Acetamido-1-(ethoxycarbonylmethyl)-2,3(1H,4H)-quinoxalinedione 52.95 g (0.2 mol) of 7-amino-1-(ethoxy-carbonylmethyl)-2,3(1H,4H)-quinoxalinedione and a spatula tip of 4-(N,N-dimethylamino)pyridine were suspended in a mixture of 500 ml of glacial acetic acid and 300 ml of tetrahydrofuran and heated to 50° C. Then 20.5 g (0.2 mol) of acetic anhydride were added dropwise and the mixture was heated at 50° C. for 2 h. The precipitate was filtered off with suction to yield 57.8 g (94%) of the product.

$^1$H-NMR (D$_6$-DMSO): δ=1.2 (3H); 2.05 (3H); 4.2 (2H); 4.9 (2H); 7.1 (1H); 7.3 (1H); 7.55 (1H); 10.0 (1H) and 12 (1H) ppm.

h) 7-Amino-1-(carboxymethyl)-6-nitro-2,3(1H,4H)-quinoxalinedione 57.5 g (0.19 mol) of 7-acetamido-1-(ethoxycarbonylmethyl)-2,3(1H,4H)-quinoxalinedione were dissolved in 575 ml of concentrated sulfuric acid. The solution was cooled to 0° C., and 19.0 g (0.19 mol) of potassium nitrate were added a little at a time. The cooling was then removed and the mixture was stirred until the reaction was complete and was then poured into 2 l of ice-water and heated on a water bath for 2 h. The pH was then adjusted with aqueous ammonia solution to about 4–5, and the precipitate was filtered off with suction. The filtrate was concentrated under reduced pressure, and the residue was purified by chromatography on silica gel (mobile phase: methanol/tetrahydrofuran/water==5:4:1+2.5% glacial acetic acid). The resulting product was combined with the first precipitate to yield 36.9 g (70%) of product.

$^1$H-NMR (D$_6$-DMSO): δ=4.5 (2H); 6.7 (1H); 7.3 (2H) and 7.7 (1H) ppm.

i) 7-Amino-1-(ethoxycarbonylmethyl)-6-nitro-2,3(1H,4H)-quinoxalinedione 30.7 g (0.11 mol) of 7-amino-1-(ethoxycarbonylmethyl)-6-nitro-2,3(1H,4H)-quinoxalinedione were suspended in 500 ml of 10% strength ethanolic sulfuric acid, and the mixture was refluxed for 2 h and then poured into ice-water. The precipitate was filtered off with suction to yield 29.3 g (87%) of the product.

$^1$H-NMR (D$_6$-DMSO): δ=1.2 (3H); 4.2 (2H); 4.8 (2H); 6.7 (1H); 7.0–7.6 (broad, 2H); 7.8 (1H) and 12.0 (1H) ppm.

j) 1-(Ethoxycarbonylmethyl)-6-nitro-7-(1-pyrrolyl)-2,3(1H,4H)-quinoxalinedione 30 g (97 mmol) of 7-amino-1-(ethoxycarbonylmethyl)-6-nitro-2,3(1H,4H)-quinoxalinedione and 16.1 g (121.5 mmol) of 2,5-dimethoxytetrahydrofuran in 500 ml of acetic acid were heated at 80° C. for 1 h. The mixture was then poured into ice-water, and the precipitate was filtered off with suction to yield 28.8 g (83%) of the product.

$^1$H-NMR (D$_6$-DMSO): δ=1.2 (3H); 4.2 (2H); 5.1 (2H); 6.2 (2H); 6.9 (2H); 7.5 (1H); 7.8 (1H) and 12.5 (1H) ppm.

EXAMPLE 53

1-(Carboxymethyl)-6-nitro-7-(1-pyrrolyl)-2,3(1H,4H)-quinoxalinedione 24.5 g (68 mmol) of 1-(ethoxycarbonylmethyl)-6-nitro-7-(1-pyrrolyl)-2,3(1H,4H)-quinoxalinedione (Example 52) were dissolved in 500 ml of tetrahydrofuran, and a solution of 6.6 g (270 mmol) of lithium hydroxide in 100 ml of water was added. The mixture was stirred at room temperature for 16 h and then the tetrahydrofuran was removed under reduced pressure, and the aqueous phase was filtered. The filtrate was acidified with 1M hydrochloric acid, and,the precipitate was filtered off with suction to yield 17.5 g (77%) of the product.

$^1$H-NMR (D$_6$-DMSO): δ=5.0 (2H); 6.2 (2H); 6.9 (2H); 7.5 (1H); 7.9 (1H); 12.5 (1H) and 13.5 (broad) ppm.

EXAMPLE 54

1-(2-Ethoxycarbonylethyl)-7-(1-pyrrolyl)-6-trifluoromethyl-2,3(1H,4H)-quinoxalinedione a) 3-(2-Nitro-4-trifluoromethylphenylamino)propionic acid 60 g (0.27 mol) of 2-chloro-1-nitro-5-trifluoromethylbenzene, 50 g (0.56 mol) of β-alanine and 41 g (0.3 mol) of potassium carbonate were refluxed in a mixture of 300 ml of dimethylformamide and 50 ml of water for 6 h. The mixture was then poured into ice-water, the aqueous phase was acidified with hydrochloric acid, and the precipitate was filtered off with suction to yield 73 g (99%) of the product.

$^1$H-NMR (D$_6$-DMSO): δ=2.7 (2H); about 3.4 (broad); 3.7 (2H); 7.3 (1H); 7.8 (1H); 8.2 (1H); 8.6 (1H) and about 12.5 (broad) ppm.

b) Ethyl 3-(2-nitro-4-trifluoromethylphenylamino)-propionate 73 g (0.26 mol) of the product 54a were suspended in 500 ml of 10% strength ethanolic sulfuric acid and heated at 80° C. until a clear solution was produced. The solution was then poured into ice-water and neutralized with aqueous ammonia and sodium bicarbonate solution, and the precipitate was filtered off with suction to yield 71.2 g (89%) of the product.

$^1$H-NMR (D$_6$-DMSO): δ=1.2 (3H); 2.7 (2H); 3.7 (2H); 4.1 (2H); 7.3 (1H); 7.8 (1H); 8.3 (1H) and 8.5 (1H) ppm.

c) Ethyl N-(2-ethoxycarbonylethyl)-N-(2-nitro-4-trifluoromethylphenyl)oxamate 40 g (0.13 mol) of the product 54b were dissolved in 200 ml of pyridine and, at room temperature, 19.6 g (0.14 mol) of ethyl oxalyl chloride were added dropwise. The mixture was stirred for 7 h and then a further 19.6 g (0.14 mol) of ethyl oxalyl chloride were added. After stirring for 16 hours, 30 ml of water were cautiously added, and the mixture was concentrated under reduced pressure. The residue was partitioned between dilute hydrochloric acid and ethyl acetate, and the organic phase was dried and concentrated under reduced pressure to yield 56 g of impure product.

$^1$H-NMR (D$_6$-DMSO): δ=0.9–1.4 (6H); 2.7 (2H); 3.8–4.3 (6H); 7.9 (1H); 8.3 (1H) and 8.5 (1H) ppm.

d) 1-(2-Ethoxycarbonylethyl)-6-trifluoromethyl-2,3(1H,4H)-quinoxalinedione 55 g (0.135 mol) of the product 54c were dissolved in 500 ml of acetic acid and heated to 80° C. Then 15.4 g (0.275 mol) of iron powder were added a little at a time, and the mixture was heated at 100° C. for 2–3 h. It was then poured into ice-water, the aqueous phase was acidified with hydrochloric acid, and the precipitate was filtered off with suction. This residue was treated with a little ethanol and again filtered off with suction to yield 30.3 g (67%) of the product.

$^1$H-NMR (D$_6$-DMSO): δ=1.2 (3H), 2.7 (2H), 4.1 (2H), 4.4 (2H), 7.5 (1H), 7.55 (1H), 7.65 (1H) and about 12.3 (1H) ppm.

e) 1-(2-Ethoxycarbonylethyl)-7-nitro-6-trifluoromethyl-2,3(1H,4H)-quinoxalinedione 35 26 g (78 mmol) of the product 54d were dissolved in 250 ml of concentrated sulfuric acid and, at 0° C., 9.5 g (94 mmol) of potassium nitrate were added a little at a time. The mixture was then stirred at room temperature for 2 h and then poured into ice-water, and the precipitate was filtered off with suction to yield 27.7 g (94%) of the product.

$^1$H-NMR (D$_6$-DMSO): δ=1.2 (3H), 2.7 (2H), 4.1 (2H), 4.4 (2H), 7.6 (1H), 8.25 (1H) and about 12.5 (1H) ppm.

f) 7-Amino-1-(2-ethoxycarbonylethyl)-6-trifluoromethyl-2,3(1H,4H)-quinoxalinedione 26 g (69 mmol) of the product 54e were dissolved in a boiling mixture of 500 ml of tetrahydrofuran and 100 ml of ethanol. This solution was slowly added dropwise to a boiling solution of 54 g (310 mmol) of sodium dithionite in 600 ml of water. The solution was then boiled for about 15 minutes and subsequently the organic solvent was removed under reduced pressure. The aqueous phase was extracted several times with ethyl acetate, and the combined organic phases were dried and concentrated under reduced pressure to yield 12.7 g (53%) of the product. Melting point 262°–263° C.

$^1$H-NMR (D$_6$-DMSO): δ=1.2 (3H), 2.7 (2H), 4.1 (2H), 4.2 (2H), about 5.5 (2H), 6.9 (1H), 7.2 (1H) and about 11.8 (1H) ppm.

g) 1-(2-Ethoxycarbonylethyl)-7-(1-pyrrolyl)-6-trifluoromethyl-2,3(1H,4H)-quinoxalinedione 6 g (17.4 mmol) of the product 54f and 3 ml (23 mmol) of 2,5-dimethoxytetrahydrofuran were heated in 150 ml of acetic acid at 80° C. for about 1 h. The mixture was then poured into ice-water, and the precipitate was filtered off with suction to yield 6.1 g (89%) of the product. Melting point 98°–120° C. (decomposition).

$^1$H-NMR (D$_6$-DMSO): δ=1.2 (3H), 2.7 (2H), 4.0 (2H), 4.4 (2H), 6.2 (2H), 6.9 (2H), 7.6 (2H) and 12.3 (1H) ppm.

EXAMPLE 55

1-(2-Carboxyethyl)-7-(1-pyrrolyl)-6-trifluoromethyl-2,3(1H,4H)-quinoxalinedione 5 g (12.7 mmol) of Example 54 were dissolved in 100 ml of tetrahydrofuran, and a solution of 0.91 g (38 mmol) of lithium hydroxide in 100 ml of water was added. The mixture was stirred for 2 h and then 20 ml of 2M hydrochloric acid were added. The organic solvent was removed under reduced pressure, and the resulting aqueous phase was extracted with ethyl acetate. The organic phase was dried and concentrated under reduced pressure to yield 4.5 g (94%) of the product. Melting point 190°–192° C.

$^1$H-NMR (D$_6$-DMSO): δ=2.6 (2H), 4.3 (2H), 6.2 (2H), 6.9 (2H), 7.55 (1H), 7.6 (1H) and 12.5 (broad, 2H) ppm.

EXAMPLE 56

1-(2-Benzylcarbamoylethyl)-7-(1-pyrrolyl)-6-trifluoromethyl-2,3(1H,4H)-quinoxalinedione 1.5 g (4 mmol) of Example 55 and 0.45 ml (4 mmol) of benzylamine were dissolved in 30 ml of anhydrous dimethylformamide, and 0.9 ml (4.2 mmol) of diphenylphosphoryl azide dissolved in 100 ml of dimethylformamide, and 1 ml (7.2 mmol) of triethylamine were successively added. The mixture was stirred at room temperature for 16 h and then poured into ice-water, the aqueous phase was acidified with dilute hydrochloric acid, and the precipitate was filtered off with suction to yield 1.47 g (74%) of the product. Melting point 234°–235° C.

$^1$H-NMR (D$_6$-DMSO): δ=2.5 (2H), 4.2 (2H), 4.4 (2H), 6.2 (2H), 6.9 (2H), 7.1 (2H), 7.2 (3H), 7.5 (1H), 7.6 (1H), 8.5 (1H) and 12.5 (1H) ppm.

EXAMPLE 57

7-(2,5-Dimethyl-1-pyrrolyl)-1-(2-ethoxycarbonylethyl)-6-trifluoromethyl-2,3(1H,4H)-quinoxalinedione 6 g (17.4 mmol) of Example 54f and 2.7 ml (23 mmol) of acetonylacetone in 100 ml of acetic acid were heated at 120°

C. for 1 h. The mixture was then diluted with a large quantity of water and extracted with ethyl acetate. The organic phase was dried and concentrated under reduced pressure. The residue was purified by chromatography on silica gel (mobile phase: toluene/tetrahydrofuran=1:1) to yield 4 g (55%) of the product.

Melting point 233°–235° C.

$^1$H-NMR (D$_6$-DMSO): δ=1.1 (3H), 2.1 (6H), 2.7 (2H), 4.0 (2H), 4.4 (2H), 5.8 (2H), 7.6 (1H), 7.65 (1H) and about 12.5 (broad) ppm.

EXAMPLE 58

1-(2-Carboxyethyl)-7-(2,5-dimethyl-1-pyrrolyl)-6-trifluoromethyl-2,3(1H,4H)-quinoxalinedione 3 g (7.1 mmol) of Example 57 were dissolved in 100 ml of tetrahydrofuran, and 0.51 g (21.3 mmol) of lithium hydroxide dissolved in 100 ml of water was added. The mixture was stirred at room temperature for about 1 h and then acidified with dilute hydrochloric acid, and the organic solvent was removed under reduced pressure. The precipitate was filtered off with suction, resulting in 2.8 g (100%) of the product. Melting point 248°–250° C. (decomposition).

$^1$H-NMR (D$_6$-DMSO): δ=1.9 (6H), 2.6 (2H), 4.3 (2H), 5.8 (2H), 7.6 (1H), 7.65 (1H) and about 12.5 (broad, 2H) ppm.

EXAMPLE 59

1-(2-Benzylcarbamoylethyl)-7-(2,5-dimethyl-1-pyrrolyl)-6-trifluoromethyl-2,3(1H,4H)-quinoxalinedione 1.2 g (3 mmol) of Example 58 were reacted with benzylamine as in Example 56 to yield 1.25 g (86%) of the product. Melting point 260°–262° C.

$^1$H-NMR (D$_6$-DMSO): δ=1.85 (6H), 2.55 (2H), 4.2 (2H), 4.4 (2H), 5.8 (2H), 7.1 (2H), 7.2 (3H), 7.5 (1H), 7.6 (1H), 8.5 (1H) and 12.4 (1H) ppm.

EXAMPLE 60

1-(Ethoxycarbonylmethyl)-9-(2,5-dimethyl-1-pyrrolyl)-benzo[f]quinoxaline-2,3(1H,4H)-dione 0.48 g (1.5 mmol) of the product 31g and 0.2 g (1.5 mmol) of 2,5-dimethoxytetrahydrofuran were refluxed in 5 ml of acetic acid for 0.5 h. The mixture was then concentrated under reduced pressure, and the residue was treated with ice-water. The precipitate was filtered off with suction to yield 0.45 g (81%) of the product.

Melting point: 239°–240° C.

$^1$H-NMR (D$_6$-DMSO): δ=1.2 (3H), 4.2 (2H), 5.15 (2H), 6.3 (2H), 7.1 (2H), 7.5 (1H), 7.6 (1H), 7.7 (2H), 8.7 (1H) and 12.5 (broad) ppm.

EXAMPLE 61

1-(Carboxymethyl)-9-(2,5-dimethyl-1-pyrrolyl)benzo[f]-quinoxaline-2,3(1H,4H)-dione 0.43 g (1.2 mmol) of Example 60 was dissolved in 5 ml of tetrahydrofuran, and a solution of 0.088 g (3.6 mmol) of lithium hydroxide in 3 ml of water was added. The mixture was stirred at room temperature for 1 h and the tetrahydrofuran was removed under reduced pressure, the residue was diluted with water and acidified with dilute hydrochloric acid, and the precipitate was filtered off with suction. Yield: 0.36 g (91%).

Melting point:>250° C.

$^1$H-NMR (D$_6$-DMSO): δ=5.1 (2H), 6.35 (2H), 7.1 (2H), 7.5–7.7 (4H), 8.7 (1H), 12.5 (1H) and about 13.3 (broad) ppm.

EXAMPLE 62

1-(2-Phenylethylcarbamoylmethyl)-6-nitro-7-pyrrolyl)-2,3(1H,4H)-quinoxalinedione 1.5 g (4.5 mmol) of Example 53 and 0.65 g (5.4 mmol) of 2-phenylethylamine were reacted as in Example 56 to yield 1.3 g (68%) of the product. Melting point 298° C. (decomposition).

$^1$H-NMR (D$_6$-DMSO): δ=2.6 (2H), 3.2 (2H), 4.8 (2H), 6.3 (2H), 6.9 (2H), 7.1–7.25 (5H), 7.3 (1H), 7.85 (1H), 8.25 (1H) and 12.5 (1H) ppm.

EXAMPLE 63

1-Cyclohexyl-7-(3-formyl-1-pyrrolyl)-6-nitro-2,3 (1H,4H)-quinoxalinedione 5.1 g (16.7 mmol) of the product 28e and 3.35 g (20.9 mmol) of 3-formyl-2,5-dimethoxytetrahydrofuran were refluxed in 100 ml of acetic acid for 2 h. The mixture was then filtered while still hot, and the filtrate was poured into a large quantity of ice-water. The precipitate was filtered off with suction to yield 5.4 g (85%) of the product. Melting point 300° C. (decomposition).

$^1$H-NMR (D$_6$-DMSO): δ=1.1–2.5 (10H), 4.5 (1H), 6.7 (1H), 7.2 (1H), 7.95 (1H), 8.0 (2H), 9.8 (1H) and 12.5 (1H) ppm.

EXAMPLE 64

1-(2-Ethylbutyl)-7-(3-formyl-1-pyrrolyl)-6-nitro-2,3 (1H,4H)-quinoxalinedione 3.0 g (9.8 mmol) of the product 5h and 1.6 g (9.8 mmol) of 3-formyl-2,5-dimethoxytetrahydrofuran were refluxed in 150 ml of acetic acid for 1 h.

The mixture was then poured into ice-water, and the precipitate was filtered off with suction to yield 0.9 g (25%) of the product. Melting point 240°–242° C. (decomposition).

$^1$H-NMR (D$_6$-DMSO): δ=0.9 (6H), 1.3 (4H), 1.8 (1H), 4.1 (2H), 6.7 (1H), 7.2 (1H), 7.5 (1H), 7.95 (1H), 8.0 (1H), 9.8 (1H) and 12.5 (1H) ppm.

EXAMPLE 65

1-Cyclohexyl-6-(3-formyl-1-pyrrolyl)-7-nitro-2,3 (1H,4H)-quinoxalinedione 4 g (13 mmol) of the product 37b, 2.3 g (14 mmol) of 3-formyl-2,5-dimethoxytetrahydrofuran and a spatula tip of 4-toluenesulfonic acid in 200 ml of dimethylformamide/toluene (1:1) were refluxed with a water trap. After the reaction was complete (TLC check), the mixture was concentrated under reduced pressure, and the residue was partitioned between ethyl acetate and water. The organic phase was dried and concentrated under reduced pressure. This residue was purified by chromatography on silica gel (mobile phase: toluene/acetone/glacial acetic acid=40/20/1) to yield 1.1 g (22%) of the product.

Melting point 176° C. (decomposition).

$^1$H-NMR (D$_6$-DMSO): δ=1.1–2.5 (10H), 4.5 (1M), 6.7 (1H), 7.2 (1H), 7.25 (1H), 8.3 (1H), 9.8 (1H) and 12.5 (1H) ppm.

EXAMPLE 66

1-(2,2-Dimethylpropyl)-7-(3-formyl-1-pyrrolyl)-6-nitro-2,3(1H,4H)-quinoxalinedione a) 4-Chloro-N-(2,2-dimethylpropyl)-2-nitroaniline 57.6 g (0.3 mol) of 2,5-dichloronitrobenzene, 26.2 g (0.3 mol) of 2,2-dimethylpropylamine, 82.9 g (0.6 mol) of potassium carbonate and 0.5 g of sodium iodide in 400 ml of dimethylformamide were heated at 80° C. for 10 h. The mixture was then added to a large amount of water and extracted with ethyl acetate. The organic phase was dried and concentrated under reduced pressure. The residue was purified by chromatography on silica gel (mobile phase: petroleum ether/toluene=16/1) to yield 32.3 g (50%) of the product. Melting point 78° C.

$^1$H-NMR (D$_6$-DMSO): δ=1.0 (9H), 3.2–3.4 (2H), 7.2 (1H) 7.55 (1H), 8.05 (1H) and 8.2 (1H) ppm.

b) 2-Amino-4-chloro-N-(2,2-dimethylpropyl)aniline 35.3 g (0.145 mol) of the product 66a were dissolved in 400 ml of methanol and, after addition of 4 g of Raney nickel, hydrogenated under 1 bar at room temperature. The mixture was then filtered, and the filtrate was concentrated under reduced pressure to yield 29.7 g (96%) of the product.

$^1$H-NMR (D$_6$-DMSO): δ=1.0 (9H), 4.1 (1H), 5.0 (2H), 6.4 (2H) and 6.5 (1H) ppm.

c) 6-Chloro-1-(2,2-dimethylpropyl)-2,3(1H,4H)-quinoxalinedione 29.2 g (0.137 mol) of the product 66b were refluxed in 400 ml of diethyl oxalate for 3 h. After cooling, the precipitate was filtered off with suction to yield 28.7 g (78%) of the product.

Melting point 298°–299° C.

$^1$H-NMR (D$_6$-DMSO): δ=0.9 (9H), 4.1 (2H), 7.1 (2H), 7.6 (2H) and 12.2 (1H) ppm.

d) 6-Chloro-1-(2,2-dimethylpropyl)-7-nitro-2,3(1H,4H)-quinoxalinedione 28.4 g (0.1 mol) of the product 66c were dissolved in 250 ml of concentrated sulfuric acid and then, at 0°–5° C., 10.8 g (0.1 mol) of potassium nitrate were added a little at a time. The mixture was then stirred at room temperature for 2 h and subsequently poured into ice, and the precipitate was filtered off with suction to yield 32.4 g (98%) of the product.

Melting point 270°–271° C.

$^1$H-NMR (D$_6$-DMSO): δ=0.9 (9H), 4.1 (2H), 7.3 (1H), 8.3 (1H) and 12.5 (1H) ppm.

e) 7-Amino-i-(2,2-dimethylpropyl)-2,3(1H,4H)-quinoxalinedione 32.1 g (0.1 mol) of the product 66d were suspended in 500 ml of isopropanol, and 65 g (1.0 mol) of ammonium formate dissolved in 250 ml of water were added. The mixture was refluxed for 1.5 h and then the isopropanol was removed under reduced pressure and the precipitate was filtered off with suction to yield 22.5 g (89%) of the product.

Melting point 260°–262° C. (decomposition).

$^1$H-NMR (D$_6$-DMSO): δ=1.0 (9H), 4.0 (2H), 5.1 (2H), 6.4 (1H), 6.7 (1H), 6.9 (1H) and 11.8 (1H) ppm.

f) 7-Acetamido-1-(2,2-dimethylpropyl)-2,3(1H,4H)-quinoxalinedione 22.3 g (90 mmol) of the product 66e and 0.1 g of 4-(N,N-dimethylamino)pyridine were dissolved in 400 ml of acetic acid, and a solution of 9.2 g (90 mmol) of acetic anhydride in 25 ml of acetic acid was added dropwise. The mixture was then stirred at 30°–40° C. for 2 h. The precipitate was filtered off with suction to yield 23.8 g (91%) of the product. Melting point 294°–295° C.

$^1$H-NMR (D$_6$-DMSO): 1.0 (9H), 2.1 (3H), 4.0 (2H), 7.1 (1H), 7.3 (1H), 8.0 (1H), 10.0 (1H) and 12.0 (1H) ppm.

g) 7-Amino-1-(2,2-dimethylpropyl)-6-nitro-2,3(1H,4H)-quinoxalinedione 23.8 g (82 mmol) of the product 66f were dissolved in 250 ml of concentrated sulfuric acid and, at 0° to 5° C., 8.3 g (82 mmol) of potassium nitrate were added a little at a time. The mixture was then stirred at room temperature for 2 h and subsequently poured into ice, and the suspension was heated on a water bath for 4 h. The precipitate was filtered off with suction to yield 19.8 g (82%) of the product. Melting point >300° C.

$^1$H-NMR (D$_6$-DMSO): δ=1.0 (9H), 3.8–4.2 (3H), 7.0 (1H), 7.7 (1H) and 11.8 (1H) ppm.

h) 1-(2,2-Dimethylpropyl)-7-(3-formyl-1-pyrrolyl)-6-nitro-2,3(1H,4H)-quinoxalinedione 8 g (27 mmol) of the product 66g and 5.5 g (34 mmol) of 3-formyl-2,5-dimethoxytetrahydrofuran in 100 ml of acetic acid were refluxed for 2 h. The mixture was then filtered and the filtrate was poured into ice-water. The precipitate was filtered off with suction and purified by chromatography on silica gel (mobile phase: toluene/acetone/acetic acid=20:10:1) to yield 5.7 g (56%) of the product.

Melting point 262°–264° C. (decomposition).

$^1$H-NMR (CDCl$_3$): δ=0.95 (5H), 4.2 (2H), 6.7 (1H), 7.1 (1H), 7.85 (1H), 7.9 (1H), 8.0 (1H), 9.8 (1H) and 12.5 (1H) ppm.

EXAMPLE 67

1-(2,2-Dimethylpropyl)-7-(3-hydroxyiminomethyl-1-pyrrolyl)-6-nitro-2,3(1H,4H)-quinoxalinedione 2 g (5.4 mmol) of Example 66, 0.75 g (11 mmol) of hydroxylammonium chloride and 0.89 g (11 mmol) of sodium acetate were refluxed in 60 ml of ethanol/water (5:1) for 2 h. After cooling, the precipitated product was filtered off with suction to yield 1.7 g (82%). Melting point 251° C. (decomposition).

$^1$H-NMR (CDCl$_3$): δ=0.95 (9H), 4.2 (2H), 6.5–6.6 (1H), 6.9+7.2 (1H), 7.5+7.6 (1H), 7.7–8.2 (3H), 10.6+11.1 (1H) and 12.4 (1H) ppm.

The $^1$H-NMR shows that an E/Z mixture is present.

EXAMPLE 68

7-(3-Cyano-1-pyrrolyl)-1-(2,2-dimethylpropyl)-6-nitro-2,3(1H,4H)-quinoxalinedione 1.57 g (4 mmol) of Example 67 were refluxed in 25 ml of acetic anhydride for 4 h. The mixture was then poured into ice-water and extracted with methylene chloride. The organic phase was dried and concentrated under reduced pressure. The residue was crystallized from methanol/ether to yield 0.55 g (63%) of the product.

Melting point: 220°–223° C.

$^1$H-NMR (D$_6$-DMSO): δ=1.0 (9H), 4.2 (2H), 6.7 (1H), 7.2 (1H), 7.75 (1H), 7.9 (1H), 8.0 (1H) and 12.5 (1H) ppm.

EXAMPLE 69

1–Cyclohexyl-7-(3-hydroxyiminomethyl-1-pyrrolyl)-6-nitro-2,3(1H,4H)-quinoxalinedione 1.75 g (4.6 mmol) of Example 65 and 0.32 g (4.6 mmol) of hydroxylammonium chloride were refluxed in 50 ml of ethanol for 2 h. The mixture was concentrated under reduced pressure, and the residue was purified by chromatography on silica gel (mobile phase: toluene/acetone/acetic acid=20/10/1) to yield 1.7 g (94%) of the product.

Melting point 234° C.

EXAMPLE 70

1-(Ethoxycarbonylmethyl)-7-(3-formyl-1-pyrrolyl)-6-trifluoromethyl-2,3(1H,4H)-quinoxalinedione a) Ethyl N-(2-nitro-4-trifluoromethylphenyl)oxamate 51.5 g (0.25 mol) of 2-nitro-4-trifluoromethylaniline, 45 ml (0.32 mol) of triethylamine and 0. 1 g of N,N-dimethylaminopyridine were dissolved in 500 ml of anhydrous tetrahydrofuran under a nitrogen atmosphere. At 0°–5° C., 44.4 g (0.32 mol) of ethyl oxalyl chloride were added dropwise and then the mixture was stirred at room temperature until reaction was complete (checked by thin-layer chromatography). The mixture was then concentrated under reduced pressure, and the residue was partitioned between water and ethyl acetate. The organic phase was dried and concentrated under reduced pressure. The crude product was recrystallized from ethanol to yield 68.2 g (89%) of the product.

$^1$H-NMR (CDCl$_3$): δ=1.5 (3H), 4.5 (2H), 8.0 (1H), 8.6 (1H), 9.05 (1H) and 12.2 (1H) ppm.

b) Ethyl N-(ethoxycarbonylmethyl)-N-(2-nitro-4-trifluoromethylphenyl)oxamate 70 g (0.23 mol) of the product 70a were dissolved in 1 l of anhydrous tetrahydrofuran under a nitrogen atmosphere. At room temperature, 34.8 g (0.31 mol) of potassium tert-butanolate was added a little at a time. The mixture was stirred for 30 minutes and then 42.1 , g (0.25 mol) of ethyl bromoacetate were added dropwise. The mixture was then stirred at room temperature for 2 h and subsequently concentrated under reduced pressure, and the residue was partitioned between ethyl acetate and water. The organic phase was dried and concentrated under reduced pressure to yield 63 g (70%) of the crude product, which was immediately processed further.

c) 1-(Ethoxycarbonylmethyl)-6-trifluoromethyl-2,3(1H,4H)-quinoxalinedione 63 g (0.16 mol) of the product 70b were dissolved in 1 l of acetic acid and refluxed while adding 54 g (0.97 mol) of iron powder a little at a time. The mixture was then heated for 1 h and subsequently cooled and filtered. The filtrate was concentrated under reduced pressure, and the residue was treated with water. The resulting solid was filtered off with suction and recrystallized from ethanol to yield 48.2 g (95%) of the product.

Melting point 250°–251° C.

$^1$H-NMR (D$_6$-DMSO): δ=1.25 (3H), 4.7 (2H), 5.0 (2H), 7.5 (3H) and 12.4 (1H) ppm.

d) 1-(Ethoxycarbonylmethyl)-7-nitro-6-trifluoromethyl-2,3(1H,4H)-quinoxalinedione g (mol) of the product 70c were dissolved in 500 ml of concentrated sulfuric acid and, at 0° C., 15 g (0.149 mol) of potassium nitrate were added a little at a time. The mixture was stirred for a further 30 minutes and then poured into ice-water. The aqueous phase was extracted with ethyl acetate. The organic phase was concentrated under reduced pressure, and the precipitate was filtered off with suction and recrystallized from ethanol to yield 45.9 g (89%) of the product.

$^1$H-NMR (D$_6$-DMSO): δ=1.25 (3H), 4.2 (2H), 5.0 (2H), 7.7 (1H), 8.25 (1H) and 12.7 (1H) ppm.

e) 7-Amino-1-(ethoxycarbonylmethyl)-6-trifluoromethyl-2,3(1H,4H)-quinoxalinedione 43 g (0.12 mol) of the product 70d were dissolved in 300 ml of dimethylformamide and, after addition of 2 g of palladium/carbon (10%), hydrogenated under 1 bar at room temperature. The mixture was then filtered, and the filtrate was concentrated under reduced pressure. The residue was treated with ethanol and filtered off with suction to yield 37.1 g (95%) of the product. Melting point >250° C.

$^1$H-NMR (D$_6$-DMSO): δ=1.25 (3H), 4.2 (2H), 4.85 (2H), 5.5 (2H), 6.6 (1H), 7.2 (1H) and 12.0 (1H) ppm.

f) 1-(Ethoxycarbonylmethyl)-7-(3-formyl-1-pyrrolyl)-6-trifluoromethyl-2,3(1H,4H)-quinoxalinedione 25 g (75.5 mmol) of the product 70e and 12 g (75.5 mmol) of 3-formyl-2,5-dimethoxytetrahydrofuran in 300 ml of acetic acid were heated at 85° C. for 1 h. The mixture was then concentrated under reduced pressure and purified by chromatography on silica gel (mobile phase: methylene chloride/acetone=3/1) to yield 20.3 g (66%) of the product. Melting point 236°–237° C.

$^1$H-NMR (D$_6$-DMSO): δ=1.2 (3H), 4.2 (2H), 5.0 (2H), 6.6 (1H), 7.05 (1H), 7.65 (1H), 7.8 (2H), 9.8 (1H) and 12.3 (1H) ppm.

EXAMPLE 71

1-(Carboxymethyl)-7-(3-formyl-1-pyrrolyl)-6-trifluoromethyl-2,3(1H,4H)-quinoxalinedione 1.2 g (2.9 mmol) of Example 70f were dissolved in 100 ml of tetrahydrofuran, and 0.21 g (8.8 mmol) of lithium hydroxide-dissolved in 15 ml of water was added. The mixture was stirred at room temperature for 2 h and then the organic solvent was removed under reduced pressure and the aqueous phase was acidified. The precipitate was filtered off with suction to yield 0.83 g (75%) of the product. Melting point >250° C.

$^1$H-NMR (D$_6$-DMSO): δ=4.9 (2H), 6.65 (1H), 7.1 (1H), 7.65 (1H), 7.75 (1H), 8.0 (1H), 9.8 (1H), 12.5 (1H) and about 13.3 (broad) ppm.

EXAMPLE 72

1-Carboxymethyl-7-(2,5-dimethyl-1-pyrrolyl)-6-trifluoromethyl-2,3(1H,4H)-quinoxalinedione a) 1-(Ethoxycarbonylmethyl)-7-(2,5-dimethyl-1-pyrrolyl)-6-trifluoromethyl-2,3(1H,4H)-quinoxalinedione (Example 23)

5.1 g (15.4 mmol) of the product 70e and 1.8 ml (15.4 mmol) of 2,5-hexanedione were refluxed in 100 ml of acetic acid for 0.5 h. The mixture was then concentrated under reduced pressure and purified by chromatography on silica gel (mobile phase: methylene chloride/methanol=10/1). The crude product was treated with water and filtered off with suction to yield 5.3 g (85%) of the product. Melting point 262°–263°C.

1H-NMR (D$_6$-DMSO): δ=1.2 (3H), 1.85 (6H), 4.15 (2H), 5.1 (2H), 5.7 (2H), 7.45 (1H), 7.7 (1H) and 12.5 (1H) ppm.

b) 1–Carboxymethyl-7-(2,5-dimethyl-1-pyrrolyl)-6-trifluoromethyl-2,3(1H,4H)-quinoxalinedione 3.3 g (8.1 mmol) of the product 72a were dissolved in 100 ml of tetrahydrofuran, and 0.58 g (24.2 mmol) of lithium hydroxide dissolved in 25 ml of water was added. The mixture was stirred at room temperature for 1 h, and then the organic solvent was removed under reduced pressure and the resulting aqueous phase was acidified with 2M hydrochloric acid. The precipitate was filtered off with suction to yield 28 g (92%) of the product. Melting point >270° C.

$^1$H-NMR (D$_6$-DMSO): δ=1.85 (6H), 5.0 (2H), 5.8 (2H), 7.4 (1H), 7.7 (1H), 12.5 (1H) and about 13.3 (broad) ppm.

EXAMPLE 73

1-Benzylcarbamoylmethyl-7-(2,5-dimethyl-1-pyrrolyl)-6-trifluoromethyl-2,3(1H,4H)-quinoxalinedione 1.6 g (4.2 mmol) of the compound of Example 72 and 0.5 ml (4.6 mmol) of benzylamine were dissolved in 50 ml of anhydrous dimethylformamide under a nitrogen atmosphere. At 0° C., 1 ml (4.6 mmol) of diphenylphosphoryl azide dissolved in 10 ml of anhydrous dimethylformamide, and 1.3 ml (9.2 mmol) of triethylamine were successively added dropwise. The mixture was then stirred at room temperature for 16 h and subsequently diluted with water, acidified and extracted with ethyl acetate. The organic phase was dried and concentrated under reduced pressure. The residue was recrystallized from ethanol to yield 1.1 g (56%) of the product. Melting point >250° C.

$^1$H-NMR (D$_6$-DMSO): δ=1.8 (6H), 4.25 (2H), 4.9 (2H), 5.8 (2H), 7.1–7.3 (5H), 7.65 (1H), 8.65 (1H) and 12.4 (1H) ppm.

EXAMPLE 74

1-Ethoxycarbonylmethyl-7-(3-hydroxyiminomethyl-1-pyrrolyl)-6-trifluoromethyl-2,3(1H,4H)-quinoxalinedione 1.2 g (2.9 mmol) of the compound from Example 70, 0.4 g (6 mmol) of hydroxylammonium chloride and 0.48 g (6 mmol) of sodium acetate in 45 ml of H$_2$O/EtOH (2:1) were refluxed for 30 minutes. The organic solvent was removed under reduced pressure, and the resulting aqueous phase was extracted with ethyl acetate. The organic phase was dried and concentrated under reduced pressure. The residue was recrystallized from ethanol to yield 1.6 g (70%) of the product. Melting point >250° C.

$^1$H-NMR (D$_6$-DMSO): δ=1.2 (3H), 4.15 (2H), 5.0 (2H), 6.6 (1H), 6.9 (1H), 7.3 (1H), 7.6–7.8,(3H), 11.1 (1H) and 12.5 (1H) ppm.

EXAMPLE 75

7-(3-Benzyloxyiminomethyl-1-pyrrolyl)-1-(ethoxycarbonylmethyl)-6-trifluoromethyl-2,3(1H,4H)-quinoxalinedione 1.1 g (2.7 mmol) of the compound of Example 70, 0.86 g (5.4 mmol) of O-benzylhydroxylammonium chloride and 0.44 g (5.4 mmol) of sodium acetate in 4.5 ml of EtOH/H$_2$O (1:2) were refluxed for 30 minutes. The ethanol was then removed under reduced pressure, and the precipitate was filtered off with suction and recrystallized from ethanol to yield 1.15 g (84%) of the product. The $^1$H-NMR shows that an E/Z mixture is present. Melting point 142°–147° C.

$^1$H-NMR (D$_6$-DMSO): δ=1.2 (3H), 4.2 (2H), 5.0 (2H), 5.1+5.2 (2H), 6.5+6.7 (1H), 7.0 (1H), 7.2–8.2 (9H) and 12.5 (1H) ppm.

EXAMPLE 76

1-Carboxymethyl-7-(3-hydroxyiminomethyl-1-pyrrolyl)-6-trifluoromethyl-2,3(1H,4H)-quinoxalinedione 1.6 g (3.8 mmol) of the compound of Example 74 were dissolved in 100 ml of tetrahydrofuran, and 0.4 g (15.1 mmol) of lithium hydroxide dissolved in 25 ml of water was added. The mixture was stirred at room temperature for 2 h and then the tetrahydrofuran was removed under reduced pressure and the aqueous phase was acidified. The precipitate was filtered off with suction.

Melting point >225° C.

$^1$H-NMR (D$_6$-DMSO): δ=4.8 (2H), 6.5 (1H), 6.9 (1H), 7.3 (1H), 7.5 (1H), 7.6 (1H), 7.7 (1H), 11.0 (1H) and 12.5 (1H) ppm.

EXAMPLE 77

7-(3-Benzyloxyiminomethyl-1-pyrrolyl)-1-carboxymethyl-6-trifluoromethyl-2,3(1H,4H)-quinoxalinedione 1.2 g (2.3 mmol) of Example 74 were hydrolyzed with 0.2 g (7 mmol) of lithium hydroxide as in Example 76 to yield 1.0 g (90%) of the product.

$^1$H-NMR (D$_6$-DMSO): δ=4.9 (2H), 5.1+5.2 (1H), 6.4+6.6 (1H), 6.9 (1H), 7.2–8.2 (9H), 12.5 (1H) and 13.5 (broad) ppm.

The $^1$H-NMR shows that an E/Z mixture is present.

EXAMPLE 78

7-(3-Cyano-1-pyrrolyl)-1-cyclohexyl-6-nitro-2,3(1H, 4H)-quinoxalinedione 1.75 g (4.4 mmol) of Example 69 were refluxed in 25 ml of acetic anhydride for 5 h. The mixture was then poured into ice-water and extracted with methylene chloride. The organic phase was washed with aqueous sodium bicarbonate solution and then dried and concentrated under reduced pressure to yield 1.2 g (70%) of the product. Melting point 304°–305° C.

$^1$H-NMR (D$_6$-DMSO): δ=1.0–2.5 (10H), 4.4 (1H), 6.7 (1H), 7.2 (1H), 7.8 (1H), 8.0 (2H) and 12.3 (1H) ppm.

EXAMPLE 79

1-Cyclohexyl-6-methylsulfonyl-7-(1-pyrrolyl)-2,3 (1H,4H)-quinoxalinedione a) 1-Cyclohexyl-6-methylsulfonyl-2,3(1H,4H)-quinoxalinedione 23 g (85.7 mmol) of N$^1$-cyclohexyl-4-mesyl-1,2-phenylenediamine (Schelz et al., Dyes and Pigments 1983, 4, 305–320) were refluxed in 200 ml of diethyl oxalate for 2 h. After cooling, the precipitate was filtered off with suction to yield 18.5 g (67%) of the product. Melting point >300° C.

$^1$H-NMR (D$_6$-DMSO): δ=1.2–2.5 (10H), 3.2 (3H), 4.5 (1H), 7.6–7.7 (2H), 7.75 (1H) and 12.3 (1H) ppm.

b) 1-Cyclohexyl-6-methylsulfonyl-7-nitro-2,3(1H,4H)-quinoxalinedione 9 g (28 mmol) of the product 79a were dissolved in 90 ml of concentrated sulfuric acid and, at 0° C., 2.7 g (31.8 mmol) of sodium nitrate were added a little at a time. The mixture was then stirred at room temperature for 3 h and subsequently poured into ice-water, and the precipitate was filtered off with suction and then purified by chromatography on silica gel (mobile phase: toluene/acetone/acetic acid= 10:10:1) to yield 3.8 g (37%) of the product. Melting point >280° C.

$^1$H-NMR (D$_6$-DMSO): δ=1.1–2.5 (10H), 3.5 (3H), 4.5 (1H), 7.8 (1H), 8.3 (1H) and 12.5 (1H) ppm.

c) 7-Amino-1-cyclohexyl-6-methylsulfonyl-2,3(1H,4H)-quinoxalinedione 2.3 g (6.3 mmol) of the product 79b were dissolved in 100 ml of tetrahydrofuran and, after addition of 0.3 g of palladium/carbon (10%), hydrogenated. The mixture was then filtered, and the filtrate was concentrated under reduced pressure to yield 2.0 g of a crude product which was immediately reacted further.

d) 1-Cyclohexyl-6-methylsulfonyl-7-(1-pyrrolyl)-2,3(1H, 4H)-quinoxalinedione g (mmol) of the product 79c and g (mmol) of 2,5-dimethoxytetrahydrofuran were refluxed in 50 ml of acetic acid for 30 minutes. The mixture was then concentrated under reduced pressure, and the residue was recrystallized from a little ethanol to yield 0.9 g (38%) of the product.

Melting point >280° C.

$^1$H-NMR (D$_6$-DMSO): δ=1.0–2.5 (10H), 3.3 (3H), 4.5 (1H), 6.25 (2H), 7.0 (2H), 7.6 (1H) and 7.7 (1H) ppm.

EXAMPLE 80

1-(Ethoxycarbonylmethyl)-7-(3-formyl-1-pyrrolyl)-6-nitro-2,3(1H,4H)-quinoxalinedione 5.0 g (1.6 mmol) of the product from Example 52i and 2.9 g (1.8 mmol) of 3-formyl-2,5-dimethoxytetrahydrofuran were introduced into 100 ml of acetic acid at 80°–90° C. The mixture was stirred for 30 minutes and then poured into ice-water, and the precipitate was filtered off with suction, to yield 5.3 g (86%) of the product.

$^1$H-NMR (D$_6$-DMSO): δ=1.2 (3H), 4.15 (3H), 4.15 (2H), 5.05 (2H), 6.7 (1H), 7.15 (1H), 7.8 (1H), 7.9 (1H), 8.0 (1H), 9.8 (1H) and 12.3 (broad) ppm.

EXAMPLE 81

7-(3-Benzylaminomethyl-1-pyrrolyl)-1-(ethoxycarbonylmethyl)-6-trifluoromethyl-2,3(1H,4H)-quinoxalinedione 1.2 g (2.9 mmol) of the compound of Example 70, 0.31 g (2.9 mmol) of benzylamine and 0.2 ml (2.9 mmol) of acetic acid were dissolved in 50 ml of ethanol and, at room temperature, 0.18 g (2.9 mmol) of sodium cyanoborohydride was added a little at a time. The mixture was stirred for 16 h and then concentrated under reduced pressure, and the organic phase was dried and finally concentrated again under reduced pressure. The residue was purified by chromatography on silica gel (mobile phase: methylene chloride/methanol=5:1) to yield 0.87 g (60%) of the product.

$^1$H-NMR (D$_6$-DMSO): δ=1.2 (3H), 3.8 (2H), 3.9 (2H), 4.1 (2H), 5.0 (2H), 6.3 (1H), 7.85 (1H), 7.9 (1H), 7.2–7.8 (7H) and 12.3 (broad) ppm.

EXAMPLE 82

7-(3-Benzyloxyiminomethyl-1-pyrrolyl)-1-(carboxymethyl)-6-nitro-2,3(1H,4H)-quinoxalinedione 1.5 g (3.9 mmol) of Example 80, 1.2 g (7.8 mmol) of O-benzylhydroxylamine hydrochloride and 0.6 g (7.8 mmol) of sodium acetate were refluxed in 45 ml of ethanol/water (1:2) for 2 h. The mixture was then diluted with water and extracted with ethyl acetate. The organic phase was dried and concentrated under reduced pressure to yield 1.7 g of an oil which was dissolved in 50 ml of tetrahydrofuran. Then 0.27 g of lithium hydroxide dissolved in 50 ml of water was added and the mixture was stirred at room temperature for 2 h. The tetrahydrofuran was then removed under reduced pressure, and the resulting aqueous phase was acidified with 2M hydrochloric acid and then extracted with ethyl acetate. The organic phase was dried and concentrated under reduced pressure. The residue was purified by chromatography on silica gel (mobile phase: methylene chloride/methanol=2/1) to yield 0.17 g (10%) of the product as E/Z mixture.

$^1$H-NMR (D$_6$-DMSO): δ=4.5+4.6 (2H), 5.1+5.15 (2H), 6.4–8.5 (11H) and 12.2 (broad) ppm.

EXAMPLE 83

7-(3-Formyl-1-pyrrolyl)-6-nitro-2,3(1H,4H)-quinoxalinedione 2.0 g (9.0 mmol) of the product 5c and 1.4 g (9.0 mmol) of 3-formyl-2,5-dimethoxytetrahydrofuran in 50 ml of acetic acid were refluxed for 1 h. The mixture was then poured into water, and the precipitate was filtered off with suction. This residue was boiled with a little active carbon and silica gel in 60 ml of dimethylformamide/tetrahydrofuran (1/5). The suspension was filtered, and the filtrate was concentrated under reduced pressure. The residue was suspended in water and filtered off with suction to yield 0.3 g (13% of theory) of the product. Melting point >250° C.

$^1$H-NMR (D$_6$-DMSO): δ=6.65 (1H), 7.1 (1H), 7.15 (1H), 7.9 (1H), 7.95 (1H), 9.7 (1H) and about 12.3 (broad) ppm.

EXAMPLE 84

1-Ethylcarbamoylmethyl-6-nitro-7-(1-pyrrolyl)-2,3(1H,4H)-quinoxalinedione 1.5 g (4.5 mmol) of Example 53 and 0.44 g (5.4 mmol) of ethylamine hydrochloride were reacted as in Example 48 to yield 0.9 g (56%) of the product.

Melting point >300° C.

$^1$H-NMR (D$_6$-DMSO): δ=1.0 (3H), 3.1 (2H), 4.8 (2H), 6.3 (2H), 7.9 (2H), 7.3 (1H), 7.9 (1H), 8.2 (1H) and 12.5 (1H) ppm.

EXAMPLE 85

1-Phenylcarbamoylmethyl-6-nitro-7-(1-pyrrolyl)-2,3(1H,4H)-quinoxalinedione 1.5 g (4.5 mmol) of Example 53 and 0.5 g (5.5 mmol) of aniline were reacted as in Example 48 to yield 0.9 g (49%) of the product.

Melting point >300° C.

$^1$H-NMR (D$_6$-DMSO): δ=5.1 (2H), 6.3 (2H), 6.9 (2H), 7.1 (1H), 7.3 (2H), 7.6 (3H), 7.8 (1H), 10.4 (1H) and 12.3 (1H) ppm.

EXAMPLE 86

1-Benzylcarbamoylmethyl-6-nitro-7-(1-pyrrolyl)-2,3(1H,4H)-quinoxalinedione 1.5 g (4.5 mmol) of Example 53 and 0.58 g (5.4 mmol) of benzylamine were reacted as in Example 48 to yield 1.2 g (63%) of the product.

Melting point >300° C.

$^1$H-NMR (D$_6$-DMSO): δ=4.3 (2H), 5.0 (2H), 6.3 (2H), 6.9 (2H), 7.2–7.5 (6H), 7.9 (1H), 8.8 (1H) and 12.5 (1H) ppm.

EXAMPLE 87

7-(3-Benzylaminomethyl-1-pyrrolyl)-1-(carboxymethyl)-6-trifluoromethyl-2,3(1H,4H)-quinoxalinedione 0.9 g (1.8 mmol) of Example 81 were dissolved in 30 ml of tetrahydrofuran, and 0.2 g (8.1 mmol) of lithium hydroxide dissolved in 25 ml of water was added. The mixture was stirred at room temperature for 2 h and then the tetrahydrofuran was removed under reduced pressure. The resulting aqueous phase was neutralized with 1M hydrochloric acid, and the precipitate was filtered off with suction to yield 0.8 g (90%) of the product.

Melting point >300° C.

$^1$H-NMR (D$_6$-DMSO): δ=3.9 (2H), 4.0 (2H), 4.65 (2H), 6.35 (1H), 6.9 (1H), 7.05 (1H), 7.2 (1H), 7.3–7.5 (5H), 7.7 (1H) and about 12 (1H) ppm.

EXAMPLE 88

1-(Ethoxycarbonylmethyl)-7-(3-hydroxymethyl-1-pyrrolyl)-6-trifluoromethyl-2,3(1H,4H)-quinoxalinedione 1.1 g (3.3 mmol) of the product 70e and 0.54 g (3.3 mmol) of 3-hydroxymethyl-2,5-dimethoxytetrahydrofuran in 70 ml of acetic acid were refluxed for 5 h. The mixture was then concentrated under reduced pressure, and the residue was dissolved in methylene chloride. The product was precipitated by adding petroleum ether and was then filtered off with suction to yield 1.3 g (45%).

Melting point >185°–186° C.

$^1$H-NMR (D$_6$-DMSO): δ=1.2 (3H), 4.15 (2H), 4.95 (2H), 5.05 (2H), 6.25 (1H), 6.9 (1H), 7.0 (1H), 7.6 (1H), 7.6 (2H) and 12.5 (broad) ppm.

EXAMPLE 89

7-(3-Benzoylaminomethyl-1-pyrrolyl)-1-(carbethoxymethyl)-6-trifluoromethyl-2,3(1H,4H)-quinoxalinedione a) 3-Benzoylaminomethyl-2,5-dimethoxytetrahydrofuran 2 g (12.4 mmol) of 2,5-dimethoxy-3-aminonmethyltetrahydrofuran and 3.4 ml (24.8 mmol) of triethylamine were dissolved in 50 ml of anhydrous tetrahydrofuran. At 0° C., 1.7 g (12.4 mmol) of benzoyl chloride dissolved in 20 ml of anhydrous tetrahydrofuran were added dropwise. The mixture was stirred for 1 h and then filtered, and the filtrate was concentrated under reduced pressure. The residue was reprecipitated from ether/petroleum ether to yield 2.4 g of impure product which was used in the next step.

b) 7-(3-Benzoylaminomethyl-1-pyrrolyl)-1-(carbethoxymethyl)-6-trifluoromethyl-2,3(1H,4H)-quinoxalinedione 1 g (3.0 mmol) of the product 70e and 1.6 g (6.0 mmol) of the product 89a were stirred in 70 ml of acetic acid at 100° C. for 30 minutes. After cooling, the precipitate was filtered off with suction and washed with water to yield 1.1 g (71%) of the product.

Melting point >210°–211° C.

$^1$H-NMR (D$_6$-DMSO): δ=1.2 (3H), 4.15 (2H), 4.35 (2H), 5.05 (2H), 6.2 (1H), 6.8 (2H), 7.4–7.6 (5H), 7.7–7.8 (2H), 8.8 (1H) and 12.5 (1H) ppm.

EXAMPLE 90

7-(3-Benzoylaminomethyl-1-pyrrolyl)-1-(carboxymethyl)-6-trifluoromethyl-2,3(1H,4H)-quinoxalinedione 1 g (1.9 mmol) of Example 89 was dissolved in 40 ml of tetrahydrofuran, and 0.14 g (5.8 mmol) of lithium hydroxide dissolved in 10 ml of water was added. The mixture was stirred at room temperature for 24 h and then acidified with 1M hydrochloric acid, and the precipitate was filtered off with suction to yield 0.8 g (85%) of the product.

$^1$H-NMR (D$_6$-DMSO): δ=4.35 (2H), 4.9 (2H), 6.25 (1H), 6.8 (1H), 6.85 (1H), 7.4–7.55 (5H), 7.9 (2H), 8.8 (1H) and 12.4 (broad) ppm.

EXAMPLE 91

7-(3-Acetylaminomethyl-1-pyrrolyl)-1-(carbethoxymethyl)-6-trifluoromethyl-2,3(1H,4H)-quinoxalinedione a) 3-Acetylaminomethyl-2,5-dimethoxytetrahydrofuran 4.0 g of 2,5-dimethoxy-3-aminomethyltetrahydrofuran and 1.75 ml of acetyl chloride were reacted as in Example 89a. 3.7 g of impure product were obtained and were immediately reacted further.

b) 7-(3-Acetylaminomethyl-1-pyrrolyl)-1-(carbethoxymethyl)-6-trifluoromethyl-2,3(1H,4H)-quinoxalinedione 1.5 g (4.5 mmol) of the product 70e were refluxed with 3.7 g of the product 91a in 70 ml of acetic acid for 30 minutes. The mixture was then concentrated under reduced pressure and the residue was recrystallized from ethanol to yield 1.6 g (79%) of the product.

Melting point >250° C.

$^1$H-NMR (D$_6$-DMSO): δ=1.2 (3H), 4.1–4.3 (3H), 4.1–4.3 (4H), 5.0 (2H), 6.15 (1H), 6.8 (2H), 7.5 (1H), 7.6 (1H), 8.2 (1H) and 12.5 (broad) ppm.

EXAMPLE 92

7-(3-Acetylaminomethyl-1-pyrrolyl)-1-(carboxymethyl)-6-trifluoromethyl-2,3(1H,4H)-quinoxalinedione 1.3 g (2.9 mmol) of Example 91 were suspended in 50 ml of tetrahydrofuran, and 0.21 g (8.6 mmol) of lithium hydroxide dissolved in 25 ml of water was added. The mixture was stirred at room temperature for 1.5 h and then the tetrahydrofuran was removed under reduced pressure, and the resulting aqueous phase was acidified with 1M hydrochloric acid. The precipitate was filtered off with suction, resulting in 1.0 g (85%) of the product.

Melting point >250°–251° C.

$^1$H-NMR (D$_6$-DMSO): δ=1.8 (3H), 4.1 (3H), 4.9 (2H), 6.2 (1H), 6.8 (2H), 7.4 (1H), 7.6 (1H), 8.1 (1H), 12.4 (1H) and 13.3 (broad) ppm.

EXAMPLE 93

1-(Carboxymethyl)-7-(3-formyl-1-pyrrolyl)-6-nitro-2,3(1H,4H)-quinoxalinedione 1.7 g (4.4 mmol) of Example 80 were dissolved in 50 ml of tetrahydrofuran and hydrolyzed with 0.32 g (13.4 mmol) of lithium hydroxide as in Example 90 to yield 1.1 g (69%) of the product.

$^1$H-NMR (D$_6$-DMSO): δ=4.9 (2H), 6.6 (1H), 7.15 (1H), 7.7 (1H), 7.9 (1H), 8.0 (1H), 9.7 (1H) and 12.8 (broad) ppm.

EXAMPLE 94

9-(3-Benzoylaminomethyl-1-pyrrolyl)-1-(ethoxycarbonylmethyl)benzo[f]quinoxaline-2,3(1H,4H)-dione 2.0 g (6.3 mmol) of the product 34g and 2.5 g (9.6 mmol) of the tetrahydrofuran derivative 89 a were heated at 100° C. in 50 ml of acetic acid for about 10 minutes. The mixture was then concentrated under reduced pressure. The residue was treated with ethanol, and the precipitate was filtered off with suction to yield 2.5 g (80%) of the product.

Melting point >250° C.

$^1$H-NMR (D$_6$-DMSO): δ=1.2 (3H), 4.15 (3H), 4.25 (2H), 5.1 (2H), 6.3 (1H), 7.0 (2H), 7.3–7.75 (7H), 7.85 (2H), 8.7 (1H), 8.85 (1H) and 12.5 (broad) ppm.

EXAMPLE 95

9-(2-Benzoylaminomethyl-1-pyrrolyl)-1-(ethoxycarbonylmethyl)benzo[f]quinoxaline-2,3(1H,4H)-dione a) 2-Benzoylaminomethyl-2,5-dimethoxytetrahydrofuran 10 g (62 mmol) of 2-aminomethyl-2,5-dimethoxytetrahydrofuran and 17 ml (123 mmol) of triethylamine were dissolved in 100 ml of anhydrous tetrahydrofuran. At 0° C., 7.2 ml (62 mmol) of benzoyl chloride were added dropwise, and the mixture was stirred at 0° C. for 1 h and then filtered, and the filtrate was concentrated under reduced pressure to yield 17 g of the crude product which was immediately reacted further.

b) 9-(2-Benzoylaminomethyl-1-pyrrolyl)-1-(ethoxycarbonylmethyl)benzo[f]quinoxaline-2,3(1H,4H)-dione 2 g (6.4 mmol) of the product 34g and 2.5 g (9.6 mmol) of the above product 95a were reacted in 100 ml of acetic acid as in Example 94 to yield 2.7 g (86%) of the product.

Melting point >206°–207° C.

$^1$H-NMR (D$_6$-DMSO): δ=1.2 (3H), 4.0–4.3 (4H), 5.0 (2H), 6.75 (2H), 6.9 (1H), 7.15 (1H), 7.2–7.7 (8H), 7.9 (1H), 8.45 (1H), 8.7 (1H) and 12.5 (broad) ppm.

EXAMPLE 96

9-(2-Benzoylaminomethyl-1-pyrrolyl)-1-(carboxymethyl)benzo[f]quinoxaline-2,3(1H,4H)-dione 1.4 g (2.8 mmol) of Example 95 and 0.2 g (8.5 mmol) of lithium hydroxide were reacted as in Example 90 to yield 1.1 g (84%) of the product.

Melting point >180° C.

$^1$H-NMR (D$_6$-DMSO): δ=4.1–4.3 (2H), 4.8 (1H), 5.0 (1H), 6.3 (2H), 6.9 (1H), 7.2 (1H), 7.3 (2H), 7.45 (1H), 7.55 (3H), 7.7 (1H), 7.8 (1H), 8.4 (1H), 12.5 (1H) and about 13.3 (broad) ppm.

We claim:

1. A method for treating a host in need of spasmolytic or anxiolytic treatment which comprises administering to said host a therapeutically effective amount of a 2,3(1H,4H)-quinoxalinedione of the formula I

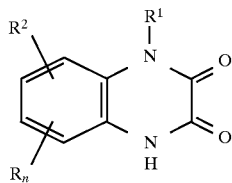

or its tautomer or enantiomer or its physiologically tolerated salt, where

R$^1$ is hydrogen, a cycloaliphatic radical having up to 8 carbons, phenyl, an alkyl radical having up to 12 carbons and which can carry one or two identical or different substituents selected from the group consisting of phenyl, cyclopentyl, cyclohexyl, —CO—R$^3$, —CO—OR$^3$, —CO—NH—R$^3$, —OR$^3$, —NR$^7$R$^8$,

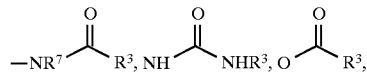

=N—OR$^3$, —CN, where R$^3$ and

R$^7$ are each, independently of one another, hydrogen, C$_1$–C$_4$-alkyl, phenyl, benzyl, 1-phenylethyl or 2-phenylethyl, and where the cycloaliphatic radical having up to 8 carbon atoms and aromatic rings present in R$^1$ can carry up to three substituents selected from the group consisting of C$_1$–C$_4$-alkyl, C$_1$–C$_4$-haloalkyl, C$_1$–C$_4$-alkoxy, C$_1$–C$_4$-haloalkoxy, halogen, nitro, cyano, —CO—OR$^9$, —CO—NH—R$^9$, —OH,

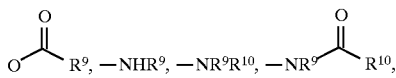

=N—OR$^9$, =O; where R$^9$ and R$^{10}$ are each, independently of one another, hydrogen, C$_1$–C$_4$-alkyl, phenyl, benzyl, 1-phenylethyl and 2-phenylethyl, R$^2$ is 1-pyrrolyl which can carry one or two of the following substituents: C$_1$–C$_4$-alkyl, phenyl, phenylsulfonyl, nitro, cyano or —CO—R$^3$, —CO—NH—R$^3$, —NH$_2$—O—R$^3$, —OR$^3$, —CH=NO—R$^3$, —C(O)—R$^3$,

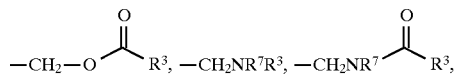

—CH=CH—R$^8$, —CH=N—R$^3$, where R$^8$ is —COOR$^3$, —CONH—R$^3$, CN or phenyl;

R is C$_1$–C$_4$-alkyl, C$_1$–C$_4$-alkoxy, trifluoromethyl, trichloromethyl, trifluoromethoxy, trichloromethoxy, fluorine, chlorine, bromine, nitro, cyano or —CO—OR$^3$, —CO—NHR$^3$, —SO$_2$R$^3$ or

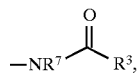

and n is an integer from 0 to 3, where the radicals R are identical or different when n is 2 or 3.

2. A method for treating a host in need of antidepressant treatment which comprises administering to said host a therapeutically effective amount of a 2,3(1H,4H)-quinoxalinedione of the formula I

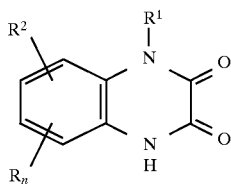

or its tautomer or enantiomer or its physiologically tolerated salt, where

R$^1$ is hydrogen, a cycloaliphatic radical having up to 8 carbons, phenyl, an alkyl radical having up to 12 carbons and which can carry one or two identical or different substituents selected from the group consisting of phenyl, cyclopentyl, cyclohexyl, —CO—R$^3$, —CO—OR$^3$, —CO—NH—R$^3$, —OR$^3$, —NR$^7$R$^8$,

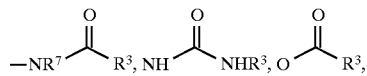

=N—OR$^3$, —CN, where R$^3$ and R$^7$ are each, independently of one another, hydrogen, C$_1$–C$_4$-alkyl, phenyl, benzyl, 1-phenylethyl or 2-phenylethyl, and where the cycloaliphatic radical having up to 8 carbon atoms and aromatic rings present in R$^1$ can carry up to three substituents selected from the group consisting of C$_1$–C$_4$-alkyl, C$_1$–C$_4$-haloalkyl, C$_1$–C$_4$-alkoxy, C$_1$–C$_4$-haloalkoxy, halogen, nitro, cyano, —CO—OR$^9$, —CO—NH—R$^9$, —OH,

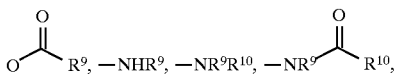

=N—OR$^9$, =O; where R$^9$ and R$^{10}$ are each, independently of one another, hydrogen, C$_1$–C$_4$-alkyl, phenyl, benzyl, 1-phenylethyl and 2-phenylethyl, R$^2$ is 1-pyrrolyl which can carry one or two of the following substituents: C$_1$–C$_4$-alkyl, phenyl, phenylsulfonyl, nitro, cyano or —CO—OR$^3$, —CO—NH—R$^3$, —NH$_2$—O—R$^3$, —OR$^3$, —CH=NO—R$^3$, —C(O)—R$^3$,

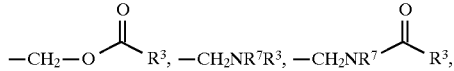

—CH=CH—R$^8$, —CH=N—R$^3$, where R$^8$ is —COOR$^3$, —CONH—R$^3$, CN or phenyl;

R is C$_1$–C$_4$-alkyl, C$_1$–C$_4$-alkoxy, trifluoromethyl, trichloromethyl, trifluoromethoxy, trichloromethoxy, fluorine, chlorine, bromine, nitro, cyano or —CO—OR$^3$, —CO—NHR$^3$, —SO$_2$R$^3$ or

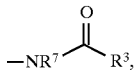

and n is an integer from 0 to 3, where the radicals R are identical or different when n is 2 or 3.

* * * * *

UNITED STATES PATENT AND TRADEMARK OFFICE
CERTIFICATE OF CORRECTION

PATENT NO.: 5,852,017

DATED: December 22, 1998

INVENTOR(S): LUBISCH et al.

It is certified that error appears in the above-identified patent and that said Letters Patent is hereby corrected as shown below:

Col. 49, claim 2, line 13, "$-NH_{2\text{-}O\text{-}R}{}^{3}$" should be -- $-NH_2-O-R^3$ --.

Signed and Sealed this

Eleventh Day of May, 1999

Attest:

Attesting Officer

Q. TODD DICKINSON

Acting Commissioner of Patents and Trademarks